(12) United States Patent
D'Lima et al.

(10) Patent No.: US 11,369,465 B2
(45) Date of Patent: Jun. 28, 2022

(54) TISSUE ARRAY PRINTING

(71) Applicant: Scripps Health, San Diego, CA (US)

(72) Inventors: Darryl D. D'Lima, San Diego, CA (US); Clifford Colwell, San Diego, CA (US)

(73) Assignee: SCRIPPS HEALTH, San Diego, CA (US)

( * ) Notice: Subject to any disclaimer, the term of this patent is extended or adjusted under 35 U.S.C. 154(b) by 376 days.

(21) Appl. No.: 14/759,398

(22) PCT Filed: Jan. 14, 2014

(86) PCT No.: PCT/US2014/011525
§ 371 (c)(1),
(2) Date: Jul. 6, 2015

(87) PCT Pub. No.: WO2014/110590
PCT Pub. Date: Jul. 17, 2014

(65) Prior Publication Data
US 2015/0351896 A1  Dec. 10, 2015

Related U.S. Application Data

(60) Provisional application No. 61/752,372, filed on Jan. 14, 2013, provisional application No. 61/785,178, filed on Mar. 14, 2013.

(51) Int. Cl.
*A61F 2/02* (2006.01)
*A61K 47/14* (2017.01)
(Continued)

(52) U.S. Cl.
CPC .............. *A61F 2/02* (2013.01); *A61F 2/022* (2013.01); *A61F 2/062* (2013.01); *A61K 35/32* (2013.01);
(Continued)

(58) Field of Classification Search
None
See application file for complete search history.

(56) References Cited

U.S. PATENT DOCUMENTS

| 4,689,186 A | 8/1987 | Bornat |
| 5,526,027 A | 6/1996 | Wade et al. |

(Continued)

FOREIGN PATENT DOCUMENTS

| EP | 1027989 A2 | 8/2000 |
| EP | 1232863 A1 | 8/2002 |

(Continued)

OTHER PUBLICATIONS

PCT/US2017/034539 International Search Report and Written Opinion dated Sep. 8, 2017.

(Continued)

*Primary Examiner* — Shaun L David
(74) *Attorney, Agent, or Firm* — Wilson Sonsini Goodrich & Rosati

(57) ABSTRACT

Methods of printing a bio-ink on a substrate are provided comprising at least one bio ink layer, said method comprising: i) positioning a printhead comprising a two-dimensional array of print nozzles within proximity of or in contact with a substrate; and ii) ejecting a bio-ink through the print nozzles onto the substrate, forming a bio ink layer, wherein the bio-ink construct comprises at least one bio-ink layer. The methods further encompass methods of printing a live tissue and methods of treating tissue defects.

24 Claims, 5 Drawing Sheets

(51) Int. Cl.
*A61F 2/06* (2013.01)
*A61K 35/32* (2015.01)
*A61K 35/33* (2015.01)
*C12M 1/26* (2006.01)
*C12M 3/00* (2006.01)
*A61F 2/08* (2006.01)
*A61F 2/28* (2006.01)

(52) U.S. Cl.
CPC .............. *A61K 35/33* (2013.01); *A61K 47/14* (2013.01); *C12M 21/08* (2013.01); *C12M 33/00* (2013.01); *A61F 2/08* (2013.01); *A61F 2/28* (2013.01); *A61F 2002/0894* (2013.01)

(56) References Cited

U.S. PATENT DOCUMENTS

| | | | |
|---|---|---|---|
| 2002/0177903 A1* | 11/2002 | Geistlich | A61F 2/0077 623/23.72 |
| 2003/0100824 A1* | 5/2003 | Warren | A61B 5/0066 600/407 |
| 2003/0175410 A1* | 9/2003 | Campbell | A61L 27/38 427/2.24 |
| 2003/0207638 A1 | 11/2003 | Bowlin et al. | |
| 2004/0237822 A1 | 12/2004 | Boland et al. | |
| 2006/0156978 A1* | 7/2006 | Lipson | B29C 64/118 118/708 |
| 2008/0038352 A1 | 2/2008 | Simpson et al. | |
| 2009/0074832 A1 | 3/2009 | Zussman et al. | |
| 2009/0117087 A1 | 5/2009 | Carroll et al. | |
| 2009/0202616 A1 | 8/2009 | Chong et al. | |
| 2009/0239302 A1* | 9/2009 | Decher | A61L 27/34 435/402 |
| 2010/0129450 A1 | 5/2010 | Atala et al. | |
| 2010/0178274 A1 | 7/2010 | Sekiya et al. | |
| 2010/0236481 A1 | 9/2010 | O'Brien et al. | |
| 2010/0331980 A1 | 12/2010 | Lee et al. | |
| 2011/0136162 A1 | 6/2011 | Sun et al. | |
| 2011/0234668 A1 | 9/2011 | Hoisington et al. | |
| 2012/0089238 A1 | 4/2012 | Kang et al. | |
| 2014/0012225 A1 | 1/2014 | Yoo et al. | |
| 2014/0051169 A1 | 2/2014 | Ganey et al. | |
| 2015/0105891 A1 | 4/2015 | Golway et al. | |
| 2015/0224291 A1 | 8/2015 | Guillemot et al. | |
| 2015/0250927 A1 | 9/2015 | Macewan | |
| 2017/0007741 A1 | 1/2017 | D'Lima et al. | |
| 2019/0275205 A1 | 9/2019 | D'Lima et al. | |

FOREIGN PATENT DOCUMENTS

| | | |
|---|---|---|
| EP | 2343415 A2 | 7/2011 |
| EP | 2458044 A1 | 5/2012 |
| GB | 2343415 A | 5/2000 |
| JP | S55057060 A | 4/1980 |
| JP | 2002254654 A | 9/2002 |
| JP | 2003180815 A | 7/2003 |
| JP | 2004513698 A | 5/2004 |
| JP | 2004216119 A | 8/2004 |
| JP | 2004523484 A | 8/2004 |
| JP | 2004254655 A | 9/2004 |
| JP | 2005278909 A | 10/2005 |
| JP | 2006051157 A | 2/2006 |
| JP | 2006122147 A | 5/2006 |
| JP | 2008514341 A | 5/2008 |
| JP | 2009039401 A | 2/2009 |
| JP | 2010501547 A | 1/2010 |
| JP | 2011255513 A | 12/2011 |
| JP | 2013512660 A | 4/2013 |
| JP | 2013523227 A | 6/2013 |
| JP | 2014514942 A | 6/2014 |
| JP | 2015535893 A | 12/2015 |
| JP | 2016513979 A | 5/2016 |
| JP | 2016519222 A | 6/2016 |
| WO | WO-0240242 A1 | 5/2002 |
| WO | WO-03028782 A1 | 4/2003 |
| WO | WO-2004087012 A1 | 10/2004 |
| WO | WO-2005023324 A1 | 3/2005 |
| WO | WO-2007102606 A1 | 9/2007 |
| WO | WO-2011107599 A1 | 9/2011 |
| WO | WO-2012113812 A1 | 8/2012 |
| WO | WO-2012136701 A1 | 10/2012 |
| WO | WO-2013093921 A1 | 6/2013 |
| WO | WO-2014110590 A1 | 7/2014 |
| WO | WO-2015017579 A1 | 2/2015 |
| WO | WO-2015066705 A1 | 5/2015 |
| WO | WO-2015138970 A1 | 9/2015 |
| WO | WO-2015175880 A1 | 11/2015 |
| WO | WO-2015179572 A1 | 11/2015 |
| WO | WO-2016164566 A1 | 10/2016 |
| WO | WO-2017040975 A1 | 3/2017 |
| WO | WO-2017080646 A1 | 5/2017 |
| WO | WO-2018185755 A1 | 10/2018 |

OTHER PUBLICATIONS

Cui et al. Accelerated myotube formation using bioprinting technology for biosensor applications. Biotechnol Lett 35(3):315-321 (2013).

Gruene et al. Laser printing of stem cells for biofabrication of scaffold-free autologous grafts. Tissue Engineering: Part C Methods 17(1):79-89 (2011).

Martin et al. Quantitative analysis of gene expression in human articular cartilage from normal and osteoarthritic joints. Osteoarthritis Cartilage 9(2):112-118 (2001).

Matsusaki et al. Three-dimensional human tissue chips fabricated by rapid and automatic inkjet cell printing. Adv Healthcare Mater 2(4):534-539 (2013).

Pauli et al. Macroscopic and histopathologic analysis of human knee menisci in aging and osteoarthritis. Osteoarthritis Cartilage 19(9):1132-1141 (2011).

PCT/US2014/011525 International Preliminary Report on Patentability dated Jul. 23, 2015.

PCT/US2015/020553 International Preliminary Report on Patentability dated Sep. 22, 2016.

Pescosolido et al. Hyaluronic acid and dextran-based semi-IPN hydrogels as biomaterials for bioprinting. Biomacromolecules 12(5):1831-1838 (2011).

Schuurman et al. Bioprinting of hybrid tissue constructs with tailorable mechanical properties. Biofabrication 3(2):021001 (7 pgs.) (2011).

Song et al. Sodium alginate hydrogel-based bioprinting using a novel multinozzle bioprinting system. Artif Org 35(11):1132-1136 (2011).

Xu et al. Hybrid printing of mechanically and biologically improved constructs for cartilage tissue engineering applications. Biofabrication 5(1): 015001 (10 pgs.) (2012).

Yamaguchi et al. Cell patterning through inkjet printing of one cell per droplet. Biofabrication 4(4):045005 (8 pgs) (2012).

Yan et al. Laser-assisted printing of alginate long tubes and annular constructs. Biofabrication 5(1):015002 (8 pgs) (2013).

International Search Report and Written Opinion for PCT/US2014/011525, dated May 13, 2014.

Cui et al., "Direct Human Cartilage Repair Using Three-Dimensional Bioprinting Technology," Tissue Eng Part A, Jun. 1, 2012, pp. 1304-1312, vol. 18, Issue 11-12.

Cui et al., "Synergistic Action of Fibroblast Growth Factor-2 and Transforming Growth Factor-beta1 Enhances Bioprinted Human Neocartilage Formation," Biotechnol Bioeng., Sep. 2012, pp. 2357-2368, vol. 109 Issue No. 9.

Cui et al., "Thermal Inkjet Printing in Tissue Engineering and Regenerative Medicine," Recent Pat Drug Deliv Formul., Aug. 2012, pp. 149-155, vol. 6, No. 2.

Ying; Li., "Electrospinning of Core-Shell Collagen Nanofibers," University of Western Ontario—Electronic Thesis and Dissertation Repository, Aug. 31, 2013.

TSUDA. Hone Kyushu Yokuseiyaku Koho to shite no Hakotsu Saibo Keisei Yokusei Inshi OCIF/OPG, Ko-RANKL Kotai, Oyobi

(56) References Cited

OTHER PUBLICATIONS sono Hoka no RANKL/RANK System Modulator J. Jpn Orthop Assoc. 78(8):1-P3-5 (2005) (w/English translation).
Bartolovic et al. The differentiation and engraftment potential of mouse hematopoietic stem cells is maintained after bio-electrospray. Analyst 135:157-164 (2010).
Brinkman et al. Photo-cross-linking of type I collagen gels in the presence of smooth muscle cells: mechanical properties, cell viability, and function. Biomacromulecules 4:890-895 (2003).
Chiu et al. Functionalization of poly(L-lactide) nanofibrous scaffolds with bioactive collagen molecules. J Biomed Mater Res 83(4):1117-1127 (2007).
Gupta et al. In Situ Photo-Cross-Linking of Cinnamate Functionalized Poly(methyl methacrylate-co-2-hydroxyethyl acrylate) Fibers during Electrospinning. Macromolecules 37(24):9211-9218 (2004).
Haslauer et al. Collagen—PCL Sheath—Core Bicomponent Electrospun Scaffolds Increase Osteogenic Differentiation and Calcium Accretion of Human Adipose-Derived Stem Cells. J Biomater Sci Polym Ed 22(13):1695-1712 (2011).
Li et al. Carbodiimide crosslinked collagen from porcine dermal matrix for high-strength tissue engineering scaffold. Int J Biol Macromol 61:69-74 (2013).
Li et al. Electrospun polyacrylonitrile nanofiber yarn prepared by funnel-shape collector Materials Letters 79:245-247 (2012).
Sahoo et al. Bio-electrospraying: A potentially safe technique for delivering progenitor cells. Biotechnol Bioeng 106(4):690-698 (2010).
Srouji et al. 3-D Nanofibrous electrospun multilayered construct is an alternative ECM mimicking scaffold. J Mater Sci Mater Med 19(3):1249-1255 (2008).
Zhang et al. Characterization of the surface biocompatibility of the electrospun PCL-collagen nanofibers using fibroblasts. Biomacromolecules 6:2583-2589 (2005).
Zhao et al. Biodegradable fibrous scaffolds composed of gelatin coated poly(epsilon-caprolactone) prepared by coaxial electrospinning. J Biomed Mater Res A 83(2):372-382 (2007).
Li. Electrospinning of Core-shell Collagen Nanofibers. Thesis. Western University Graduate & Postdoctoral Studies (126 pgs) (2013).
Shields et al. Mechanical Properties and Cellular Proliferation of Electrospun Collagen Type II. Tissue Engineering 10(9/10):1510-1517 (2004).
Stankus et al. Fabrication of cell microintegrated blood vessel constructs through electrohydrodynamic atomization. Biomaterials. 28:2738-2746 (2007).
U.S. Appl. No. 15/125,749 Office Action dated May 2, 2019.
U.S. Appl. No. 15/125,749 Office Action dated Sep. 20, 2018.
Xu et al. Experimental and modeling study of collagen scaffolds with the effects of crosslinking and fiber alignment. Int J Biomater 2011:172389 (2011).
U.S. Appl. No. 15/125,749 Office Action dated Feb. 10, 2020.
Liu et al. Photochemical crosslinked electrospun collagen nanofibers: synthesis, characterization and neural stem cell interactions. J Biomed Mater Res A 95:276-282 (2010).
Wang et al. Fabrication and characterization of heparin-grafted poly-L-lactic acid-chitosan core-shell nanofibers scaffold for vascular gasket. ACS Appl Mater Interfaces 5:3757-3763 (2013).
Wu et al. In vivo fast equilibrium microextraction by stable and biocompatible nanofiber membrane sandwiched in microfluidic device. Anal Chem 85:11524-11531 (2013).
O'Connell et al. Development of the Biopen: a handheld device for surgical printing of adipose stem cells at a chondral wound site. Biofabrication 8(1):015019 (2016).
Bone and Joint Regeneration Technology. National Institute of Advanced Industrial Science and Technology Today. Available at https://www.aist.go.jp/Portals/0/resource_images/aist_e/research_results/publications/pamphlet/today/b_regeneration_e.pdf (16 pgs) (2006).
Kim et al. The development of genipin-crosslinked poly(caprolactone) (PCL)/gelatin nanofibers for tissue engineering applications. Macromol. Biosci. 10:91-100 (2010).
Lee et al. Development of a composite vascular scaffolding system that withstands physiological vascular conditions. Biomaterials 29:2891-2898 (2008).
Torricelli e al. Co-electrospun gelatin-poly(L-lactic acid) scaffolds: modulation of mechanical properties and chondrocyte response as a function of composition. Materials Science and Engineering: C 36:130-138 (2014).
U.S. Appl. No. 15/125,749 Office Action dated Nov. 13, 2020.
Grogan et al. In vitro model for the study of necrosis and apoptosis in native cartilage. J. Pathol. 198:5-13 (2002).
Grogan et al. Mesenchymal progenitor cell markers in human articular cartilage: normal distribution and changes in osteoarthritis. Arthritis Res. Ther. 11:R85 (2009).
PCT/US2015/020553 International Search Report and Written Opinion dated Jun. 8, 2015.
Roberts et al. Immunohistochemical study of collagen types I and II and procollagen IIA in human cartilage repair tissue following autologous chondrocyte implantation. Knee 16:398-404 (2009).
U.S. Appl. No. 15/125,749 Office Action dated May 28, 2021.

\* cited by examiner

Direction of movement of print-head

Area to be printed

No movement of print-head

TISSUE ARRAY PRINTING

CROSS-REFERENCE

This application is a U.S. National Stage entry of International Application No. PCT/US14/11525, filed Jan. 14, 2014, which claims priority from U.S. Provisional Patent Application No. 61/785,178, entitled "Tissue Array Printing," filed Mar. 14, 2013, and U.S. Provisional Patent Application No. 61/752,372, also entitled "Tissue Array Printing," filed Jan. 14, 2013, both of which are incorporated herein in their entirety.

SUMMARY OF THE INVENTION

Disclosed herein, in some embodiments, are methods of printing a bio-ink construct comprising at least one bio ink layer, said method comprising: i) positioning a printhead comprising a two-dimensional array of print nozzles within proximity of or in contact with a substrate; and ii) ejecting a bio-ink through the print nozzles onto the substrate, forming a bio ink layer, wherein the bio-ink construct comprises at least one bio-ink layer. In some embodiments, the bio-ink construct comprises a plurality of bio-ink layers. In some embodiments, printing the bio-ink construct does not require movement of the printhead. In some embodiments, printing the plurality of bio-ink layers does not require movement of the printhead. In some embodiments, the print nozzles in the two-dimensional array of print nozzles are independently controlled and actuated to print an individual droplet. In some embodiments, the print nozzles are fired simultaneously. In some embodiments, the print nozzles are fired in a specified sequence. In some embodiments, the bio-ink comprises a plurality of cells, a component of extracellular matrix, a cellular material, a cellular component, a growth factor, a peptide, a protein, a synthetic molecule, a synthetic polymer, or a combination thereof. In some embodiments, the plurality of cells comprises cells selected from chondrocytes, connective tissue fibroblasts, tendon fibroblasts, bone marrow reticular tissue fibroblasts, nonepithelial fibroblasts, pericytes, osteoprogenitor cells, osteoblasts, osteoclasts, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, kidney cells, hepatic cells, pancreatic cells, immune cells, stem cells, germ cells, nurse cells, interstitial cells, stellate cells and progenitors thereof. In some embodiments, the plurality of cells comprises cells selected from chondrocytes, connective tissue fibroblasts, tendon fibroblasts, bone marrow reticular tissue fibroblasts, nonepithelial fibroblasts, pericytes, osteoprogenitor cells, osteoblasts, osteoclasts, progenitors thereof and combinations thereof. In some embodiments, the plurality of cells comprises chondrocytes. In some embodiments, the bio-ink comprises polyethylene glycol, polyethylene glycol macromers, alginate, Matrigel, type II collagen, hyaluronan, or chondroitin sulfate or combinations thereof. In some embodiments, the method further comprises polymerizing the bio-ink on the substrate. In some embodiments, the method further comprises ejecting the bio-ink through the print nozzles and polymerizing the bio-ink simultaneously. In some embodiments, the method further comprises ejecting the bio-ink through the print nozzles and polymerizing the bio-ink sequentially. In some embodiments, the method further comprises printing the bio-ink construct onto a tissue defect. In some embodiments, the tissue defect is selected from a damaged tissue, eroded tissue, diseased tissue or degenerated tissue. In some embodiments, the tissue defect is in a tissue selected from skin, bone, muscle, nerves, brain, eye, pancreas, spleen, cartilage, thyroid, adipose, sinus, esophagus, kidney, heart, lung, intestine, stomach, colon, rectum, breast, ovary, uterus, cervix, prostate, bladder or liver. In some embodiments, the tissue defect is selected from a vascular defect, an osteochondral defect, an epidermal defect, a muscular defect, an intestinal defect, a neuronal defect, a reproductive defect, a pancreatic defect, or an ocular defect. In some embodiments, the tissue defect comprises an osteochondral defect. In some embodiments, the osteochondral defect is in a joint selected from a knee joint, a hip joint, an elbow joint, a shoulder joint, a wrist joint, a spine joint, a finger joint, an ankle joint, or a foot joint. In some embodiments, the osteochondral defect is in a knee joint. In some embodiments, the bio-ink construct is a live tissue. In some embodiments, the bio-ink construct is printed on or in an individual in need thereof.

Also, disclosed herein, in some embodiments, is a system comprising a controller and a printhead, wherein the printhead comprises a two-dimensional array of print nozzles. In some embodiments, the controller controls the printhead. In some embodiments, the controller is hand-held or mountable. In some embodiments, the controller controls printhead parameters selected from: temperature; back-pressure; drops per nozzle; frequency of drop rate; number of nozzles in use; and firing energy, or a combination thereof. In some embodiments, the controller controls resolution, viscosity, cell concentration, physiological temperature and speed of printing. In some embodiments, the controller controls firing energy. In some embodiments, the firing energy includes pulse energy, pulse width, length of gap between pulses, and voltage. In some embodiments, the controller comprises a controller tip. In some embodiments, the controller tip contains at least one printhead.

Also disclosed herein, in some embodiments, is a printhead comprising a two-dimensional array of print nozzles. In some embodiments, the printhead comprises a row of print nozzles. In some embodiments, the printhead comprises at least 5 nozzles. In some embodiments, the printhead comprises about 6-20 nozzles. In some embodiments, a spacing between the print nozzles in the row of print nozzles is between about 5 micrometers and about 200 micrometers, between about 5 micrometers and about 100 micrometers, between about 50 micrometers and about 200 micrometers, between about 1 micrometers and about 50 micrometers, or between about 200 micrometers and about 400 micrometers. In some embodiments, the printhead comprises two rows of print nozzles. In some embodiments, the distance between the two rows of print nozzles is between about 5 micrometers and about 500 micrometers. In some embodiments, the distance between the two rows of print nozzles is between about 200 micrometers and about 400 micrometers. In some embodiments, each row of the two rows of print nozzles comprises 10 print nozzles. In some embodiments, the spacing between the print nozzles in each row of the two rows of print nozzles is about 169 µm. In some embodiments, the spacing between the two rows of print nozzles is about 340 µm. In some embodiments, each row of the two rows of print nozzles comprises 12 print nozzles. In some embodiments, the spacing between the print nozzles in each row of the two rows of print nozzles is about 141 µm. In some embodiments, the spacing between the two rows of print nozzles is about 300 µm. In some embodiments, each row of the two rows of print nozzles comprises 16 print nozzles. In some embodiments, the spacing between the print nozzles in each row of the two rows of print nozzles is about 84 µm. In some embodiments, the spacing between the two rows of print nozzles is about 230 µm. In some embodiments, a print nozzle in the two-dimensional array of print nozzles permits a drop volume between about 2 picoliters and about 220 picoliters. In some embodiments, the printhead prints a resolution of at least about 10 dpi, at least about 50 dpi, at least about 75 dpi, at least about 100 dpi, at least about 125 dpi, at least about 150 dpi, at least about 200 dpi, at least about 300 dpi, at least about 400 dpi, at least about 500 or more dpi, or about 1000 or more dpi. In some embodiments, the printhead comprises a resolution of at least about 100 dots per inch (dpi). In some embodiments, the printhead further comprises a temperature control apparatus.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
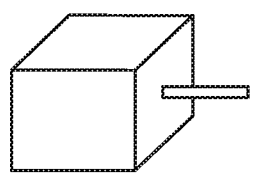
FIG. 1A depicts a printhead with a single nozzle.
Figure 1B:
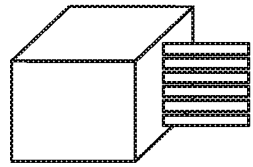
FIG. 1B depicts a printhead with a linear array of nozzles.
Figure 1C:
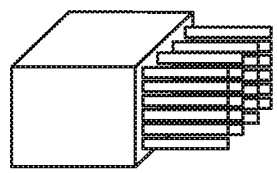
FIG. 1C depicts a printhead with a two-dimensional array of nozzles.
Figure 1D:
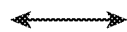
FIG. 1D exemplifies the necessity of moving a single nozzle printhead in two directions in order to print a specific two-dimensional area.
Figure 1D:
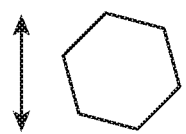
Figure 1E:
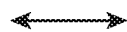
FIG. 1E exemplifies the necessity of moving a linear array in one direction in order to print a specific two-dimensional area.
Figure 1E:
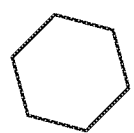
Figure 1F:
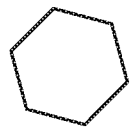
FIG. 1F exemplifies how a two-dimensional array does not require movement in order to print a specific two-dimensional area.
Figure 2A:
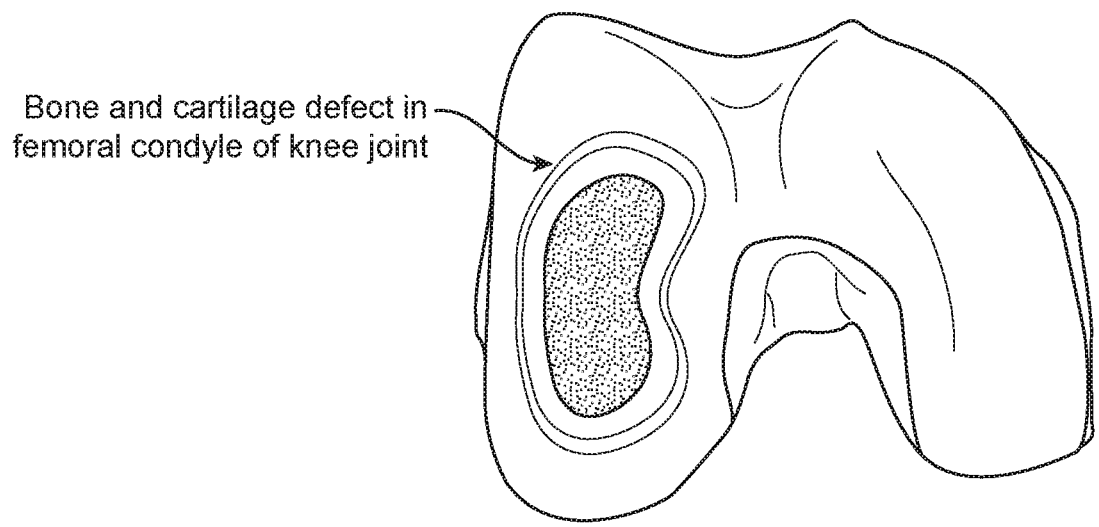
FIG. 2A depicts a bone with a cartilage defect in a femoral condyle of a knee joint.
Figure 2B:
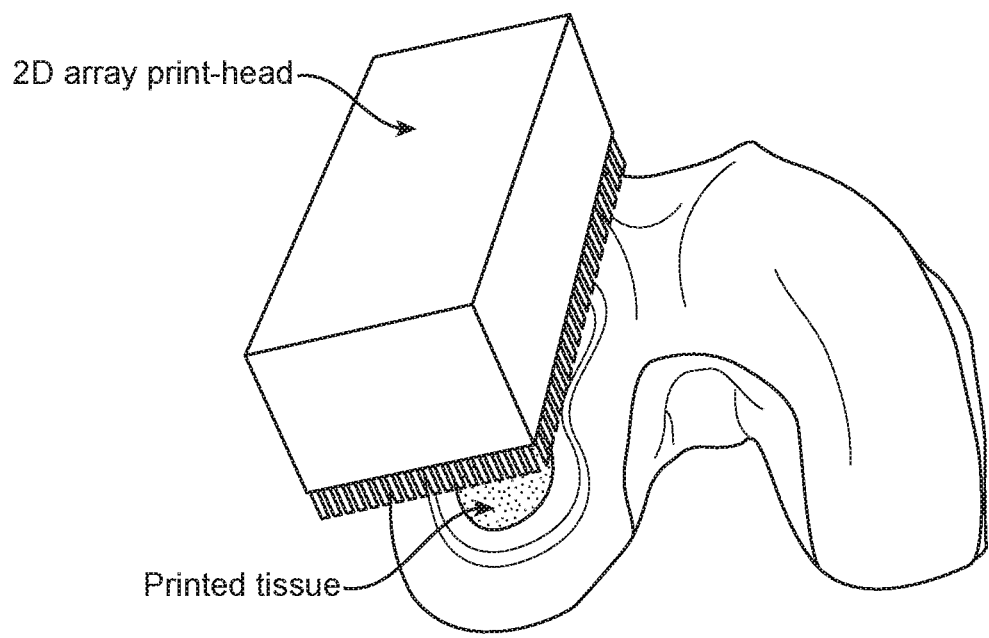
FIG. 2B exemplifies use of a two-dimensional array printhead to print tissue into an osteochondral defect of a knee joint.
Figure 3A:
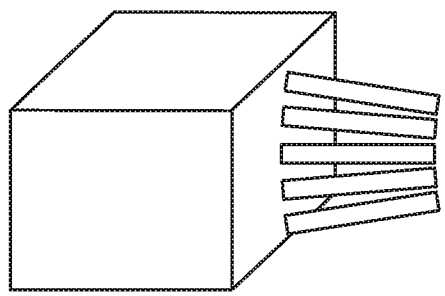
FIG. 3A depicts a linear array of converging print nozzles.
Figure 3D:
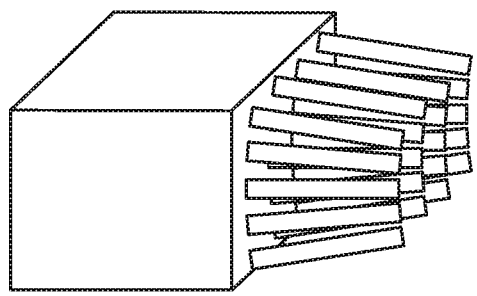
FIG. 3D depicts a two dimensional array of converging print nozzles.
Figure 3B:
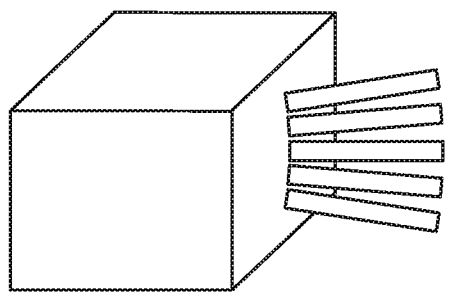
FIG. 3B depicts a linear array of diverging print nozzles.
Figure 3E:
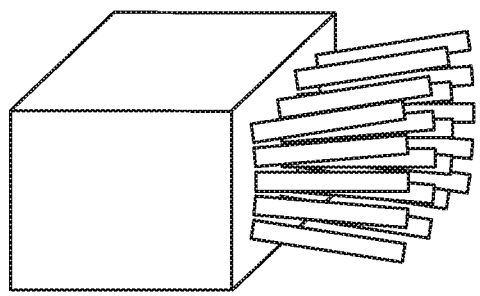
FIG. 3E depicts a two dimensional array of diverging print nozzles.
Figure 3C:
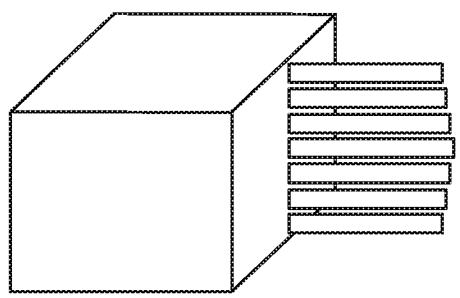
FIG. 3C depicts a linear array of print nozzles, wherein the levels of the individual print nozzles are not all in the same plane. Shown here are print nozzles that are deeper in the center.
Figure 3F:
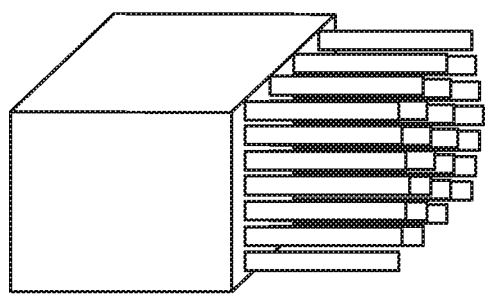
FIG. 3F depicts a two dimensional array of print nozzles, wherein the level of individual print nozzles are not all in the same plane.
Figure 4A:
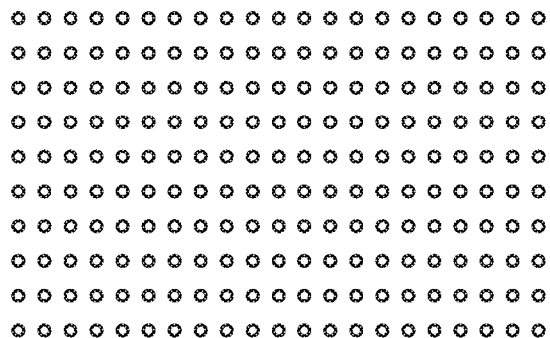
FIG. 4A exemplifies print nozzles evenly distributed in a rectangular shape.
Figure 4B:
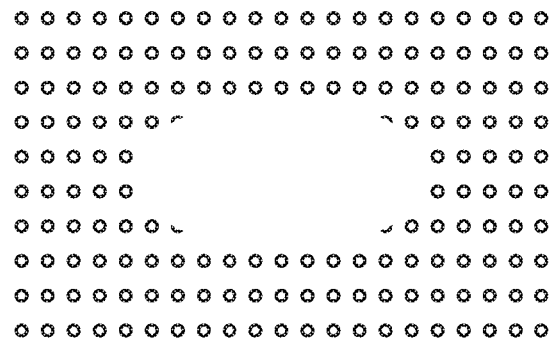
FIG. 4B exemplifies print nozzles distributed with one or more masks (an empty space devoid of print nozzles).
Figure 4C:
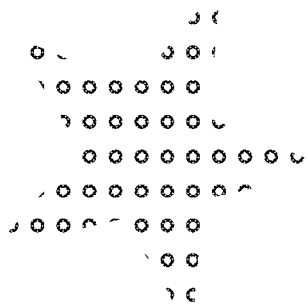
FIG. 4C exemplifies print nozzles distributed in a star shape.
Figure 4D:
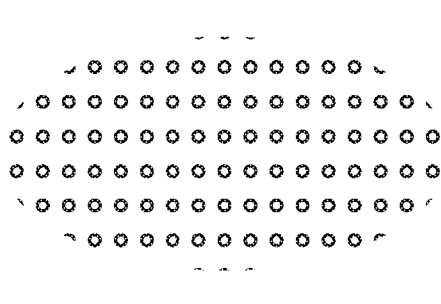
FIG. 4D exemplifies print nozzles distributed in an elliptical shape.
Figure 4E:
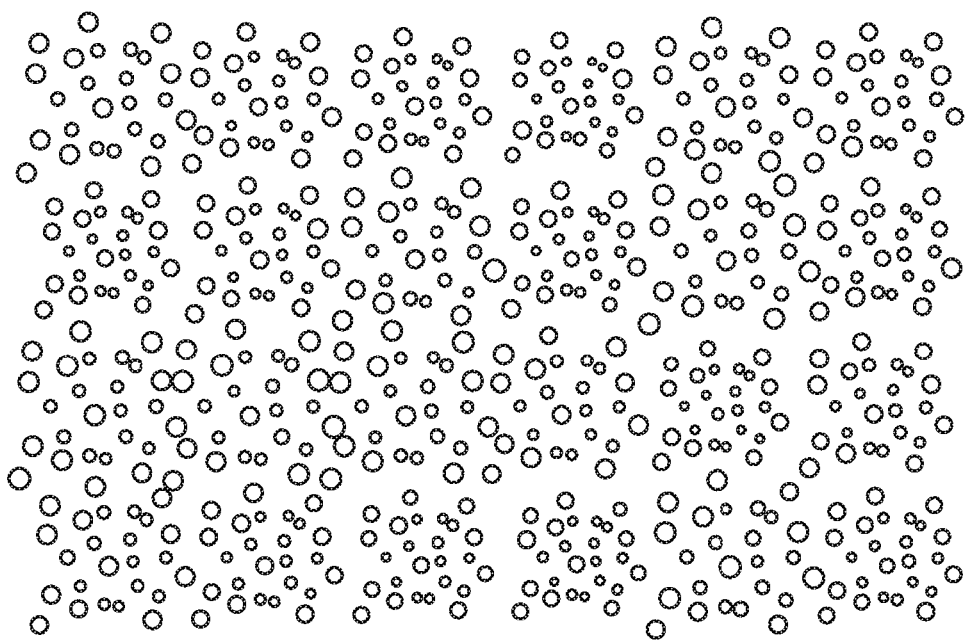
FIG. 4E exemplifies individual print nozzles of different sizes and diameters, distributed in various locations, as well as each print nozzle containing a different bioink, different cell type, different molecules, bioactive factors, matrix components, and/or pharmacologic agent.

Inkjet printing is a printing technique that reproduces digital pattern information onto a substrate with ink drops. Existing printheads either use a single nozzle that is moved in two-dimensions to print a single droplet at a time or a linear array of nozzles that are moved in one-dimension in order to print a two-dimensional area.

Disclosed herein are methods of using inkjet printing to fabricate tissues and organs, employing an inkjet printhead with a two dimensional array of print nozzles that ejects a bio-ink onto a substrate. A printhead with a two-dimensional array does not require movement of the printhead during printing, thereby increasing the precision of bioprinting by avoiding splashing of the bio-ink. In some embodiments, the substrate is a tissue defect in a living organism. Furthermore, in some embodiments, the nozzles are arranged in a variety of configurations that have the ability to conform to curved and complex surfaces.

Disclosed herein, in some embodiments, are methods of printing a bio-ink construct comprising at least one bio ink layer, said method comprising: i) positioning a printhead comprising a two-dimensional array of print nozzles within proximity of or in contact with a substrate; and ii) ejecting a bio-ink through the print nozzles onto the substrate, forming a bio ink layer, wherein the bio-ink construct comprises at least one bio-ink layer. In some embodiments, the bio-ink construct comprises a plurality of bio-ink layers. In some embodiments, printing the bio-ink construct does not require movement of the printhead. In some embodiments, printing the plurality of bio-ink layers does not require movement of the printhead. In some embodiments, the print nozzles in the two-dimensional array of print nozzles are independently controlled and actuated to print an individual droplet.

Further, disclosed herein, in some embodiments, are systems comprising a controller and a printhead, wherein the printhead comprises a two-dimensional array of print nozzles. In some embodiments, the system implements the methods disclosed herein.

Disclosed herein, in some embodiments, is a printhead comprising a two-dimensional array of print nozzles. In some embodiments, the printhead implements the methods disclosed herein.

Further disclosed herein, in some embodiments, is a method of producing a live tissue comprising: i) positioning a printhead comprising a two-dimensional array of print nozzles within proximity of a tissue culture substrate; and ii) ejecting a bio-ink comprising cells through a two-dimensional array of print nozzles onto the tissue culture substrate.

Disclosed herein, in some embodiments, is a method of treating a tissue defect comprising: i) positioning a printhead comprising a two-dimensional array of print nozzles within proximity of the tissue defect; and ii) ejecting a bio-ink comprising a plurality of cells through the two dimensional array of print nozzles onto the defect.

Certain Terminology

As used herein, a "bio-ink" refers to a composition suitable for bioprinting comprising a biopolymer and/or a plurality of cells. In some embodiments, bio-ink comprises cell solutions, cell aggregates, cell-comprising gels, proteins, multicellular bodies, or tissues.

As used herein, "chondrocytes" includes chondrocytes, articular chondrocytes, fibrochondrocytes, chondroblasts, chondrocyte precursors, chondrocyte progenitors, mesenchymal stem cells, osteoblasts, immature chondrocytes, cartilage cells, chondrogenic cells, osteogenic cells, osteoprogenitor cells, connective tissue fibroblasts, tendon fibroblasts, and cells that support the growth or differentiation of such cells.

The terms "individual," "patient," and "subject" are used interchangeably. As used herein, they mean any mammal. In some embodiments, the mammal is a human. In some embodiments, the mammal is a non-human. None of the terms require or are limited to situation characterized by the supervision (e.g. constant or intermittent) of a medical professional (e.g. a doctor, a registered nurse, a nurse practitioner, a physician's assistant, an orderly, or a hospice worker).

As used herein, a "substrate" refers to any material onto which a bio-ink is be printed. In some embodiments, the substrate is a live tissue. In some embodiments, the substrate is a support material. In some embodiments the support material is ceramic. In some embodiments, the substrate is a polymer. In some embodiments, the substrate is an extracellular matrix. In some embodiments, the substrate is a gel. In some embodiments, the substrate is a liquid. In some embodiments, the substrate is a liquid reservoir. In some embodiments, the substrate is a combination of one or more of a ceramic, a polymer, a support material, a live tissue, an extracellular matrix, a gel and a liquid.

Disclosed herein, in some embodiments, are methods of printing a bio-ink construct on to a substrate, comprising: i) positioning a printhead comprising a two-dimensional array of print nozzles within proximity of a substrate; and ii) ejecting a bio-ink through the print nozzles onto a substrate to form a bio-ink construct. In some embodiments, the method further comprises printing a bio-ink layer. In some embodiments, the method further comprises printing a plurality of bio-ink layers. The methods disclosed herein, in some embodiments, employ a printhead comprising a two-dimensional array of print nozzles, and accordingly, the methods disclosed herein do not require a mechanism to move the printhead across a two-dimensional area. In some embodiments, the two-dimensional area is larger than the printhead and the method further comprises moving the printhead a smaller distance than a conventional printhead. In some embodiments, once the printhead is positioned, printing proceeds without motion of the printhead. In some embodiments, this facilitates the speed of printing and eliminates motion of the liquid bio-ink in the printhead which, in certain instances, is associated with undesirable effects such as cell damage or splashing. In some embodiments, the printhead is positioned more than once within proximity of the substrate prior to printing. In some embodiments, the printhead is positioned only once within the proximity of the substrate prior to printing. In some embodiments, the printhead is positioned about 2, 3, 4, 5, 6, 7, 8, 9, 10, 11, 12, 13, 14, 15, 16, 17, 18, 19, 20, 25, 30 35, 40, 45, 50, 55, 60, 70, 80, 90 or 100 times within proximity of the substrate prior to printing. In some embodiments, the printhead is positioned within proximity of the substrate more than 100 times prior to printing. In some embodiments, the method disclosed herein further comprises sterilizing the printhead. In some embodiments, the printhead is sterilized with ultraviolet light. In some embodiments the printhead is sterilized with ultraviolet light for at least two hours. In some embodiments, the nozzles are sterilized with a solution. In some embodiments, the solution comprises ethanol. In some embodiments, the solution comprises about 70% ethanol, about 75% ethanol, about 80% ethanol, about 85% ethanol, about 90% ethanol, about 95% ethanol, or about 100% ethanol. In some embodiments, the distance between the printhead and the substrate is about 5 µm, about 10 µm, about 25 µm, about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, 850 µm, 900 µm, about 950 µm, about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm or about 5 cm. In some embodiments, the distance between the printhead and the substrate is less than 1 mm. In some embodiments, the distance between the printhead and the substrate is greater than 5 cm. In some embodiments, the distance between the printhead and the substrate is about 1-2 mm. In some embodiments, the printhead is in contact with the substrate. In some embodiments, the print nozzles are actuated to print individual droplets of bio-ink. In some embodiments, each print nozzle is simultaneously actuated. In some embodiments, each print nozzle is independently controlled. In some embodiments, a 2-dimensional shape is printed by simultaneously firing the print nozzles that are required to create any shape. In some embodiments, a complex 3-dimensional shape is constructed from layers of 2-dimensional shapes. In some embodiments, the methods disclosed herein further comprise modification of the 3-dimensional shape after bioprinting. In some embodiments, modification of the 3-dimensional shape comprises removing a portion of bioprinted material. In some embodiments, the method further comprises combining multiple 3-dimensional shapes. In some embodiments, the method further comprises printing a 2-dimensional shape by firing the print nozzles that are required to create the two-dimensional shape. In some embodiments, the print nozzles are fired in a specified sequence. In some embodiments, the print nozzles are fired simultaneously. In some embodiments, two or more print nozzles are fired simultaneously. In some embodiments, all the print nozzles are fired simultaneously. In some embodiments, the methods of bioprinting further comprise polymerizing the bio-ink. In some embodiments, polymerizing the bio-ink comprises applying a specified temperature or chemical to the bio-ink. In some embodiments, the method comprises polymerizing the bio-ink as it is printed on the substrate. In some embodiments, the method comprises photopolymerizing the bio-ink as it is printed on the substrate. In some embodiments, the method comprises polymerizing the bio-ink after it is printed on the substrate. In some embodiments, the method comprises photopolymerizing the bio-ink after it is printed on the substrate. In some embodiments, the methods of bioprinting further comprise gelling the bio-ink. In some embodiments, gelling the bio-ink comprises applying a specified temperature or chemical to the bio-ink. In some embodiments, the bio-ink undergoes gelatinization. In some embodiments, gelatinization is induced by a change pH, a change in temperature, coulombic interactions, covalent bonding, non-covalent interactions, or polymerization. In some embodiments, polymerizing the bio-ink comprises cross-linking the polymers in the bio-ink. In some embodiments, cross-linking the polymers in the bio-ink comprises chemical cross-linking. In some embodiments, cross-linking the polymers in the bio-ink occurs after the bio-ink is printed. In some embodiments, cross-linking the polymers in the bio-ink and printing occur simultaneously. In some embodiments, cross-linking the polymers in the bio-ink comprises cross-linking with a free radical initiator. In some embodiments, cross-linking the polymers in the bio-ink comprises crosslinking with thiol or amine moieties. In some embodiments, the bio-ink turns into a solid during the printing process. In some embodiments, the method comprises polymerization or degradation of the bio-ink by exposure to light. In some embodiments, light is used to partially degrade a bioprinted tissue. In some embodiments, time, wavelength, and light intensity of light exposure are varied. In some embodiments, degradation or polymerization are paused by shuttering the light. In some embodiments, the gel continues polymerizing or degrading once light exposure resumes. In some embodiments, the method comprises adding a photoinitiator to the bio-ink. In some embodiments, the photoinitiator is added at a final concentration of about 0.01%, 0.02%, 0.03%, 0.04%, 0.05%, 0.1%, 0.15%, 0.2%, 0.25%, 0.3%, 0.35%, 0.4%, 0.45%, 0.5%, 0.6%, 0.7%, 0.8%, 0.9% or about 1% w/v gel. In some embodiments, the photoinitiator is added at a final concentration of about 0.05% w/v gel. In some embodiments, the method further comprises removing gel components (e.g. non-cellular components, non-ECM components) after bioprinting by physical, chemical, or enzymatic means. In some embodiments, the gel components are removed by degradation of the gel components. In some embodiments, the methods disclosed herein result in printed cells that produce elevated glycosaminoglycan relative to respective cells in two dimensional cell culture and/or elevated proteoglycans relative to cells in two dimensional cell culture. In some embodiments, the average cell viability of printed cells is at least 60%, at least 65%, at least 70%, at least 75%, at least 80%, at least 85%, at least 90%, at least 95%, at least 98% or at least 99%. In some embodiments, the average cell viability of printed cells is about 90%. In some embodiments, the average cell viability of printed cells is about 100%. Disclosed herein, in some embodiments, is a method of producing a live tissue comprising: i) positioning a printhead comprising a two-dimensional array of print nozzles within proximity of a substrate; and ii) ejecting a bio-ink comprising cells through a two-dimensional array of print nozzles onto the substrate. In some embodiments, the substrate is a tissue culture substrate. In some embodiments, the substrate is a subject. In some embodiments, the substrate is a dish, a collector, a platform, a scaffold, a matrix, a gel, a ceramic, a metal, a plastic, a wax or a paper. In some embodiments, the live tissue is produced by printing a plurality of bio-ink layers. In some embodiments, each bio-ink layer comprises one or more cells. In some embodiments, a bio-ink layer comprises two or more cells. In some embodiments, a plurality of bio-ink layers is printed on to or in a tissue defect. In some embodiments, a plurality of bio-ink layers is printed directly into or on to an animal. In some embodiments, a plurality of bio-ink layers is printed directly into or on to a human. In some embodiments, the plurality of bio-ink layers is bioprinted adjacently. In some embodiments, the plurality of bio-ink layers is bioprinted separately and combined after bioprinting. In some embodiments, one or more cells of each bio-ink layer are adjacent to one or more cells of an adjacent bio-ink layer. In some embodiments, the bio-ink layers are the same dimension. In some embodiments, the bio-ink layers are each independently a suitable dimension. In some embodiments, the method comprises printing 2, 3, 4, 5, 6, 7, 8, 9, 10, 20, 30, 40, 50, 100 or more bio-ink layers. In some embodiments, the thickness of each layer of the plurality of bio-ink layers is independently about 10 µm, about 12 µm, about 14 µm, about 16 µm, about 18 µm, about 20 µm, about 30 µm, about 40 µm, about 50 µm, about 60 µm, about 70 µm, about 80 µm, about 90 µm, about 100 µm, about 125 µm, about 150 µm, about 175 µm, about 200 µm, about 225 µm, about 250 µm, about 275 µm, about 300 µm, about 325 µm, about 350 µm, about 375 µm, about 400 µm, about 425 µm, about 450 µm, about 500 µm, about 525 µm, about 550 µm, about 575 µm, about 600 µm, about 625 µm, about 650 µm, about 675 µm, about 700 µm, about 725 µm, about 750 µm, about 775 µm, about 800 µm, about 825 µm, about 850 µm, about 875 µm, about 900 µm, about 925 µm, about 950 µm, about 975 µm, or about 1 mm. In some embodiments the thickness of each layer of the plurality of bio-ink layers or live tissue of a construct is independently less than about 10 µm, less than about 12 µm, less than about 14 µm, less than about 16 µm, less than about 18 lam, less than about 20 µm, less than about 22 µm, less than about 24 µm, less than about 26 µm, less than about 28 µm or less than about 30 µm at its thinnest point. In some embodiments, the method further comprises bioprinting vascular cells. In some embodiments, bioprinting vascular cells results in formation of a blood vessel or a portion thereof. In some embodiments, the live tissue will be vascularized by surrounding tissue. In some embodiments, the method of producing the live tissue further comprises bioprinting extracellular matrix components. In some embodiments, the method of producing the live tissue further comprises bioprinting vascular cells and extracellular matrix components. In some embodiments, bioprinting vascular cells and extracellular matrix comprises bioprinting endothelial cells, smooth muscle cells and fibrin. In some embodiments, the method further comprises printing cartilage. In some embodiments, the water content of the cartilage is greater than about 20%, about 30%, about 40%, about 50%, about 60%, about 70%, about 72%, about 74%, about 75%, about 76%, about 77%, about 78%, about 79%, about 80%, about 81%, about 82%, about 83%, about 84%, about 85%, about 87%, or about 90%. In some embodiments, the water content of the cartilage is about 80%. In some embodiments, the compressive modulus of the cartilage is between about 500 kPa and about 1000 kPa. In some embodiments, the compressive modulus of the printed cartilage is about 100 kPa, 200 kPa, 250 kPa, 300 kPa, 350 kPa, 375 kPa, 400 kPa, 425 kPa, 450 kPa, 475 kPa, 500 kPa, 525 kPa, 550 kPa, 575 kPa, 600 kPa, 625 kPa, 650 kPa, 675 kPa, 700 kPa, 725 kPa, 750 kPa, 775 kPa, 800 kPa, 825 kPa, 850 kPa, 875 kPa, 900 kPa, 925 kPa, 950 kPa, 975 kPa, 1000 kPa, 1100 kPa, 1200 kPa, 1300 kPa, 1400 kPa, 1500 kPa, 1700 kPa, 1800 kPa, 2000 kPa. In some embodiments, the compressive modulus is more than 1000 kPa. In some embodiments, the compressive modulus of the printed cartilage is less than 500 kPa. In some embodiments, the compressive modulus of the printed cartilage is about 400 kPa. In some embodiments, the printhead prints one or more bio-inks. In some embodiments, the printhead prints only one bio-ink. In some embodiments, the printhead prints about 2, about 3, about 4, about 5, about 6, about 7, about 8, about 9, about 10, about 12, about 14, about 16, about 18, about 20, about 25, about 30, about 35, about 40, about 45, about 50, about 55, about 60, about 65, about 70, about 75, about 80, about 85, about 90, about 95 or about 100 bio-inks. In some embodiments, the printhead prints more than 100 bio-inks. In some embodiments, the bio-ink comprises a plurality of cells. In some embodiments, the cell density of bio-ink is about 1 cell/pL, about 10 cells/pL, about 100 cells/pL, about 1 cell/nL, about 10 cells/nL, about 100 cells/nL, about 1 cell/µL, about 10 cells/µL, about 100 cells/µL, about 1000 cells/µL, about 10,000 cells cells/µL, about 100,000 cells/µL. In some embodiments, the cell density of the bio-ink is about $2\times10^6$ cells/mL, about $3\times10^6$ cells/mL, about $4\times10^6$ cells/mL, about $5\times10^6$ cells/mL, about $6\times10^6$ cells/mL, about $7\times10^6$ cells/mL, about $8\times10^6$ cells/mL, about $9\times10^6$ cells/mL, about $10\times10^6$ cells/mL, about $15\times10^6$ cells/mL, about $20\times10^6$ cells/mL, about $25\times10^6$ cells/mL, about $30\times10^6$ cells/mL, about $35\times10^6$ cells/mL, about $40\times10^6$ cells/mL, about $45\times10^6$ cells/mL, or about $50\times10^6$ cells/mL. In some embodiments, the plurality of cells comprises one cell type. In some embodiments, the plurality of cells comprises a combination of cell types. In some embodiments, the plurality of cells comprises more than one cell type. In some embodiments, the plurality of cells comprises about 2, about 3, about 4, about 5, about 6, about 7, about 8, about 9, about 10, about 12, about 14, about 16, about 18, about 20, about 25, about 30, about 35, about 40, about 45, about 50, about 55, about 60, about 65, about 70, about 75, about 80, about 85, about 90, about 95 or about 100 cell types. In some embodiments, the bio-ink comprises more than 100 cell types. In some embodiments, the plurality of cells comprises chondrocytes, chondroprogenitor cells, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, vascular smooth muscle cells kidney cells, pancreatic cells, immune cells, stem cells, germ cells, nurse cells, interstitial cells, stellate cells liver cells, gastrointestinal cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblasts, Schwann cells, adipose cells, bone cells, bone marrow cells, cartilage cells, pericytes, mesothelial cells, cells derived from endocrine tissue, stromal cells, progenitor cells, lymph cells, endoderm-derived cells, ectoderm-derived cells, mesoderm-derived cells, pericytes, or progenitors thereof and/or a combination thereof. In some embodiments, the plurality of cells comprises chondrocytes. In some embodiments, the plurality of cells comprises chondroblasts. In some embodiments, the plurality of cells comprises mesenchymal stem cells. In some embodiments, the plurality of cells comprise connective tissue fibroblasts, tendon fibroblasts, bone marrow reticular tissue fibroblasts, nonepithelial fibroblasts, pericytes, osteoprogenitor cells, osteoblasts, or osteoclasts or any combination thereof. In some embodiments, the plurality of cells comprises articular chondrocytes. In some embodiments, the plurality of cells is selected from stem cells, progenitor cells, totipotent cells, pluripotent cells, induced pluripotent stem cells, undifferentiated cells, differentiated cells, differentiating cells, trans-differentiating cells, cells from an adult, cells from a child, germ cells, circulating cells, resident cells, adherent cells, malignant cells, tumor cells, proliferating cells, quiescent cells, senescent cells, apoptotic cells, cytokine-producing cells, migrating cells, or a combination thereof. In some embodiments, the bio-ink comprises a plurality of cells that express cell adhesion molecules. In some embodiments, cell adhesion molecules are selected from one or more of an adherin, a cadherin, a calsyntenin, a claudin, a cluster differentiation protein, a contactin, an immunoglobulin, an integrin, a lectin, a nectin, an occludin, a vinculin, a porimin, a podoplanin, a podocalyxin, a periostin, a neurotrimin, a neurexin, and a selectin. In some embodiments, the cell adhesion molecule is a receptor. In some embodiments, the cell adhesion molecule is a transmembrane protein. In some embodiments, the plurality of cells comprises a genetic mutation. In some embodiments, the plurality of cells comprises a naturally-occurring genetic mutation. In some embodiments, the naturally-occurring genetic mutation is a germline genetic mutation or a somatic genetic mutation. In some embodiments, the plurality of cells comprises an induced genetic mutation. In some embodiments, the induced genetic mutation comprises a random genetic mutation or a targeted genetic mutation. In some embodiments, one or more genes in the plurality of cells comprise a genetic mutation. In some embodiments, 2, 3, 4, 5, 6, 7, 8, 9 or 10 genes in the plurality of cells comprise a genetic mutation. In some embodiments, more than 10 genes in the plurality of cells comprise a genetic mutation. In some embodiments, a gene comprises a plurality of genetic mutations. In some embodiments, the plurality of cells has been genetically modified. In some embodiments, the plurality of cells is transfected with a nucleic acid. In some embodiments, the cells have been infected by a virus comprising a nucleic acid. In some embodiments, the plurality of cells has been transduced by a virus comprising a nucleic acid. In some embodiments, the virus is selected from a retrovirus, adenovirus or adeno-associated virus. In some embodiments, the nucleic acid is selected from a vector, a plasmid, a gene, a non-coding nucleic acid, an exon, an intron, a double stranded DNA, a single stranded DNA, a RNA, a siRNA or a miRNA. In some embodiments, the nucleic acid is a gene. In some embodiments, the gene is a eukaryotic gene. In some embodiments, the gene is a prokaryotic gene. In some embodiments, the nucleic acid encodes a label or an affinity tag. In some embodiments, the plurality of cells comprises one or more labels. In some embodiments, the one or more labels comprises a fluorescent probe. In some embodiments, the fluorescent probe is selected from a CellTrace or CellTracker (Life Technologies, Carlsbad, Calif., USA). In some embodiments, the label comprises a fluorescent tag. In some embodiments, the fluorescent tag is mPlum, mCherry, tdTomato, mStrawberry, J-Red, DsRed-monomer, mOrange, mKO, mCitrine, Venus, YPet, EYFP, Emerald EGFP, CyPet, mCFPm, Cerulean, T-Sapphire, GFP or YFP. In some embodiments the plurality of cells comprises an affinity tag. In some embodiments, the affinity tag is a peptide. In some embodiments, the peptide is myc-tag, c-myc tag, FLAG-tag, His-tag, polyhistidine tag, HA-tag, V5, VSVG, softag 1, softag 3, express tag, S tag, fluorescein isothiocyanate (FITC), dinitrophenyl, trinitrophenyl, peridinin chlorophyll protein complex, biotin, phycoerythrin (PE), streptavidin, avidin, horse radish peroxidase (HRP), palmitoylation, nitrosylation, alkaline phosphatase, glucose oxidase, glutathione-S-transferase (GST), SUMO tag, thioredoxin, poly (NANP), poly-Arg, calmodulin binding protein, PurF fragment, ketosteroid isomerase, PaP3.30, TAF12 histone fold domain, maltose binding protein, or a fragment thereof. In some embodiments, the plurality of cells is from a tissue bank. In some embodiments, the plurality of cells is frozen or previously frozen. In some embodiments, the plurality of cells are harvested or isolated from a donor tissue. In some embodiments, the donor tissue is harvested from a live animal. In some embodiments, the donor tissue is derived from a monkey, an ape, a gorilla, a chimpanzee, a cow, a horse, a dog, a cat, a goat, a sheep, a pig, a rabbit, a chicken, a turkey, a guinea pig, a rat or a mouse. In some embodiments, the donor tissue is synthetic. In some embodiments, the plurality of cells is harvested from a live human donor. In some embodiments, the plurality of cells is derived from the patient. In some embodiments, the donor tissue is harvested from a cadaver. In some embodiments, the plurality of cells is harvested from a cadaver. In some embodiments, wherein the plurality of cells is harvested from a cadaver, the plurality of cells is harvested less than about 1 hour, less than about 2 hours, less than about 4 hours, less than about 6 hours, less than about 12 hours, less than about 24 hours, less than about 36 hours, less than about 48 hours, less than about 72 hours after death. In some embodiments, the plurality of cells is harvested from a cadaver less than about 72 hours after death. In some embodiments, the plurality of cells is harvested from a cadaver between 22 h and 72 h after death. In some embodiments, the plurality of cells is treated with an antibiotic and/or an antimycotic after or while they are isolated or harvested. In some embodiments, the antibiotic is penicillin, streptomycin, actinomycin D, ampicillin, blasticidin, carbenicillin, cefotaxime, fosmidomycin, gentamicin, kanamycin, neomycin, polymyxin B, or any combination thereof. In some embodiments, the antimycotic is amphotericin B, nystatin, natamycin or any combination thereof. In some embodiments, the plurality of cells is propagated or maintained in a cell culture media after they are isolated and before they are bioprinted. In some embodiments, cell culture media comprises essential nutrients, growth factors, salts, minerals, vitamins, platelet-rich plasma, or a combination thereof. In some embodiments, particular ingredients are selected to enhance cell growth, differentiation or secretion of specific proteins. In some embodiments, cell culture media comprises cellular differentiation agents. In some embodiments, the plurality of cells is cultured with a supernatant or conditioned media from another population of cells in cell culture. In some embodiments, the plurality of cells are cultured in an atmosphere of about 1%, about 2%, about 3%, about 5%, about 7%, about 10% or about $O_2$. In some embodiments, cells are cultured in an atmosphere of about 1%, about 2%, about 3%, about 4%, about 5%, about 6%, about 7%, about 8%, about 9% or about 10% $CO_2$. In some embodiments, cells are cultured at a temperature of about 30° C., about 32° C., about 33° C., about 34° C., about 35°, about 36° C., about 37° C., about 38° C., about 39° C., about 40° C. or about 42° C. In some embodiments, human chondrocytes are preferably cultured at approximately 37° C. with humidified air containing 5% CO2, media changed about every four days. In some embodiments, the plurality of cells are used for bioprinting when they grow to about 10%, about 20%, about 30%, about 40%, about 50%, about 60%, about 70%, about 80%, about 90%, about 100% confluence. In some embodiments, the plurality of cells comprises human chondrocytes. In some embodiments, human chondrocytes are used for bioprinting when they grow to about 80% to 90% confluence. In some embodiments, the plurality of cells comprises chondrocytes, fibrochondrocytes or chondrocyte progenitors. In some embodiments, the chondrocytes are maintained in a cell culture comprising a growth factor. In some embodiments, the chondrocytes are maintained in a cell culture media comprising TGF-β and FGF-β. In some embodiments, the chondrocytes are cultured in a three dimensional cell culture. In some embodiments, the three dimensional cell culture comprises a polymer, a protein, a synthetic peptide or an extracellular matrix component. In some embodiments, the three dimensional cell culture comprises an alginate, an agarose, a collagen, a laminin, a fibronectin, a tenascin, an elastin, a proteoglycan, a glycosaminoglycan, an extracellular matrix component. In some embodiments, the bio-ink comprises a cell culture medium. In some embodiments, cell culture media is selected from Balanced Salts, Dulbecco's Modified Eagle's Medium, Dulbecco's Modified Eagle's Medium/Nutrient F-12 Media, Ham's F-10 Media, Ham's F-12 Media, Minimum Essential Medium Eagle, Medium 199, RPMI-1640 Medium, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium further comprises a biological serum. In some embodiments, the serum is fetal bovine serum, fetal calf serum, fetal goat serum or horse serum. In some embodiments, the biological serum content of the cell culture medium is about 0.5% v/v, about 1% v/v, about 2% v/v, about 5% v/v, about 10% v/v, about 15% v/v, about 20% v/v, about 50% v/v, about 99% v/v, about 100% v/v. In some embodiments, the cell culture medium comprises a buffering agent. In some embodiments the buffering agent is selected from MES, ADA, PIPES, ACES, MOPSO, MOPS, BES, TES, HEPES, DIPSO, Acetamidoglycine, TAPSO, POPSO, HEPPSO, HEPPS, Tricine, Glycinamide, Bicine or TAPS. In some embodiments, the bio-ink comprises a growth factor, a protein, a chemical, a biochemical factor, a polysaccharide, a carboxylic acid, an enzyme, a protease, a therapeutic agent, or any combination thereof. In some embodiments, the growth factor is selected from Adrenomedullin (AM), Angiopoietin (Ang), Autocrine motility factor, Bone morphogenetic proteins (BMPs), Brain-derived neurotrophic factor (BDNF), Colony-stimulating factor (CSF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), insulin, Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta(TGF-β), Tumor necrosis factor-alpha(TNF-α), Vascular endothelial growth factor (VEGF), placental growth factor (PlGF), Foetal Bovine Somatotrophin (FBS), IL-1, IL-2, IL-3, IL-4, IL-5, IL-6, IL-7 or a combination thereof. In some embodiments, the bio-ink comprises TGF-β1 and FGF2. In some embodiments, the bio-ink comprises a biochemical factor. In some embodiments, the biochemical factor is selected from an anticoagulant, albumin, selenium, an amino acid, a vitamin, a hormone, a mineral, or any combination thereof. In some embodiments, the bio-ink comprises a protein. In some embodiments, the protein is a kinase, a hormone, a cytokine, a chemokine, an anti-inflammatory factor, a pro-inflammatory factor, an apoptotic factor or a steroid. In some embodiments, the bio-ink comprises a protease. In some embodiments, the bio-ink comprises a collagenase, a matrix metalloproteinase, a trypsin, a thrombase or any combination thereof. In some embodiments the bio-ink comprises a nuclease. In some embodiments, the bio-ink comprises a polysaccharide. In some embodiments, the polysaccharide is a glycosaminoglycan. In some embodiments, the glycosaminoglycan is heparin. In some embodiments, the bio-ink comprises salicylic acid. In some embodiments, the bio-ink comprises a lipid or a fatty acid. In some embodiments, the fatty acid is selected from palmitic acid, oleic acid, linolenic acid, omega-3 fatty acid or any combination thereof. In some embodiments, the bio-ink comprises a therapeutic agent. In some embodiments, the therapeutic agent is selected from an antibiotic and/or an antimycotic. In some embodiments, the antibiotic is penicillin, streptomycin, actinomycin D, ampicillin, blasticidin, carbenicillin, cefotaxime, fosmidomycin, gentamicin, kanamycin, neomycin, polymyxin B, or a combination thereof. In some embodiments, the antimycotic is amphotericin B, nystatin, natamycin or a combination thereof. In some embodiments, the therapeutic agent is selected from an anti-inflammatory therapeutic agent. In some embodiments, the anti-inflammatory therapeutic agent is a non-steroidal anti-inflammatory therapeutic agent. In some embodiments, the non-steroidal anti-inflammatory therapeutic agent is a cyclooxygenase (COX) inhibitor. In some embodiments, the COX inhibitor is selected from a COX1 inhibitor, COX2 inhibitor or combination thereof. In some embodiments, the anti-inflammatory therapeutic agent comprises a steroid. In some embodiments, the steroid is a glucocorticoid. In some embodiments, the glucocorticoid is dexamethasone. In some embodiments, the bio-ink comprises an extracellular matrix or a component thereof. In some embodiments, the bio-ink comprises collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, heparin, gelatin, elastin, fibronectin, fibrin, fibrinogen, laminin, proteoglycans, or a combination thereof. In some embodiments, the extracellular matrix is derived from a human, a cow, a horse, a sheep, a goat, a chimpanzee, a monkey, a rat, a pig, a mouse, a rabbit or a synthetic reaction. In some embodiments, the bio-ink is a gel. In some embodiments, the gel comprises a biogel or a hydrogel. In some embodiments, the biogel or hydrogel comprises a polymer. In some embodiments, the bio-ink comprises a polymer. In some embodiments, the polymer is polyethylene glycol (PEG), a PEG macromer, polyethylene glycol methacrylate (PEGMA), polyethylene dimethacrylate (PEGDMA), poly (hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide or a combination thereof. In some embodiments, the gel comprises a PEGDMA hydrogel. In some embodiments, the PEGDMA polymer is 10% w/v hydrogel. In some embodiments, the PEGDMA polymer is 20% w/v hydrogel. In some embodiments, the gel does not comprise a polymer. In some embodiments, PEG macromers comprise reactive chain ends such as acrylate, methacrylate, allyl ether, maleimide, vinyl sulfone, NHS ester and vinyl ether groups. In some embodiments, the alcohol chain ends of PEG are esterified using acid chlorides (e.g., acryloyl chloride, methacryloyl chloride) in the presence of base. In some embodiments, PEG chain ends are etherified under basic conditions by reaction with alkyl halides such as 2-chloroethyl vinyl ether or allyl bromide. In some embodiments, acrylate, methacrylate, vinyl sulfone, maleimide, vinyl ether and allyl ether are capable of step growth network formation or polymerization. In some embodiments, polymerization of macromers is initiated using redox-generated radicals (e.g., ammonium persulfate and TEMED), or radicals generated with light. In some embodiments, the bio-ink further comprises alginate, Matrigel, hyaluronan, fibrinogen, chondroitin sulfate, glycerol, cellulose, agarose, gelatin, chitosan, paraffin, silica, fibrin or a combination thereof. In some embodiments, the gel comprises a peptide, an amino acid, a dipeptide, a proteoglycan, a glycoprotein, a surfactant, a starch, or a combination thereof. In some embodiments, the bio-ink comprises fibrin. In some embodiments, the bio-ink is photopolymerizable. In some embodiments, the bio-ink is photodegradable. In some embodiments, the gel comprises photo-releasable factors. In some embodiments, photo-releasable factors are selected from cells, growth factors, proteases, ligands, hormones, extracellular matrix, cytokines, anti-inflammatory factors, pro-inflammatory factors, adhesion molecules, or a combination thereof. In some embodiments, photo-releasable factors are used to form a feature of the bioprinted tissue (e.g. vasculature). In some embodiments, the gel comprises a PEG with a degradable ester linkage. In some embodiments, the bio-ink comprises a factor that is attached to a component of the gel or the extracellular matrix. In some embodiments, the factor is released by hydrolysis or enzymolysis of a bond that attaches the factor to the component of the gel or extracelluar matrix. In some embodiments, the factor is released by hydrolysis or enzymolysis of the gel component or the extracellular matrix. In some embodiments, the factor is released from the gel component or the extracellular matrix by an enzyme. In some embodiments, the enzyme is present in the defect or substrate. In some embodiments, the bio-ink comprises the enzyme. In some embodiments, the enzyme is a protease. In some embodiments, the protease is a serine protease, a threonine protease, a cysteine protease, an aspartate protease, a glutamic acid protease, a metalloprotease, an exopeptidase, an endopeptidase, a trypsin, a chymotrypsin, a pepsin, a papain, an elastase, a carboxypeptidase, an aminopeptidase, a thrombin, a plasmin, a cathepsin or snake venom. In some embodiments, the factor released is a therapeutic agent or a growth factor. In some embodiments, the growth factor induces angiogenesis upon release.

Figure 5:
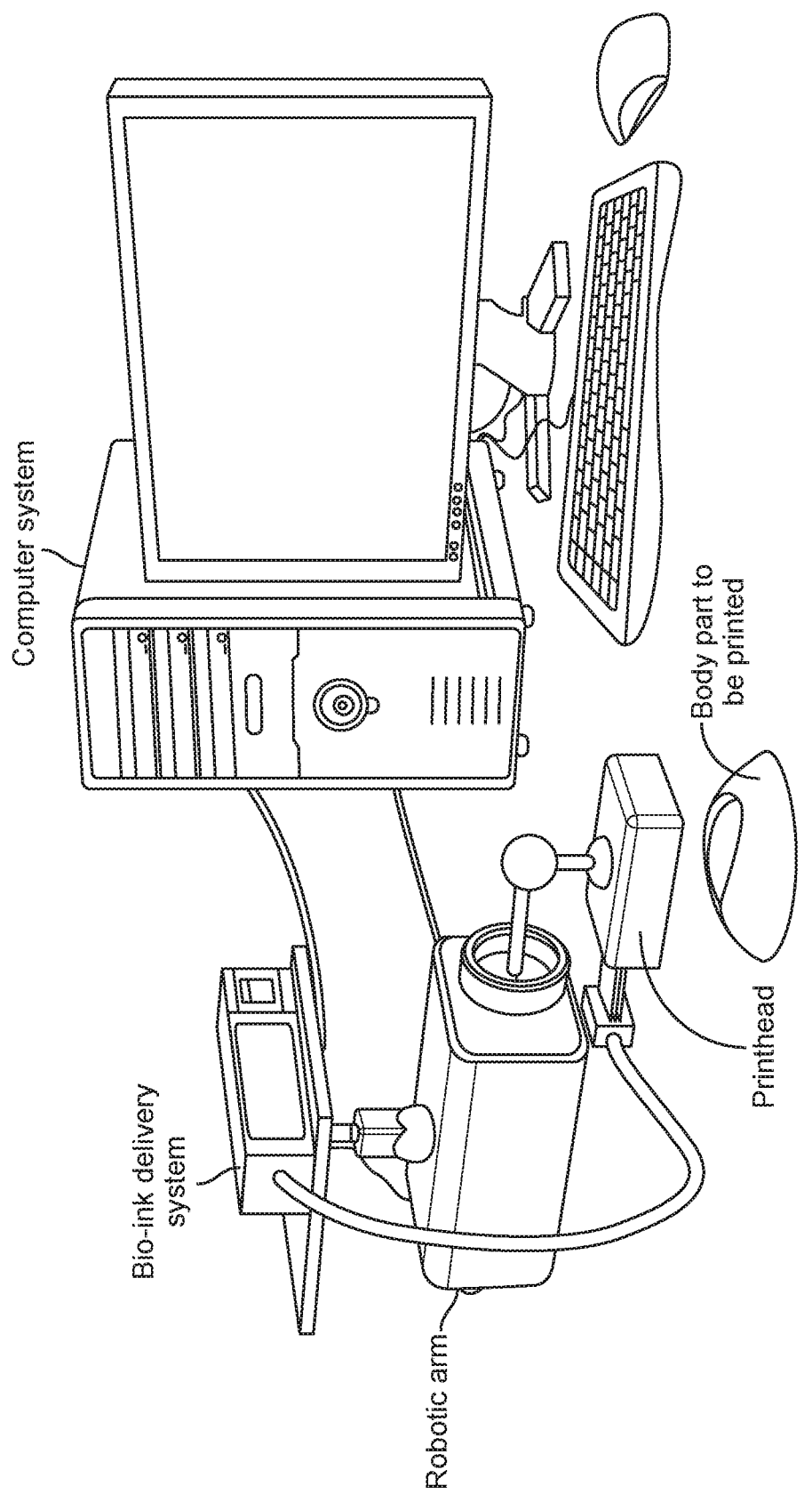
FIG. 5 exemplifies a direct bioprinting system. The printhead is connected to the robotic arm which is controlled by a computer. A bio-ink delivery system delivers the bio-ink to the printhead. The printhead is positioned over the part to be printed. The computer controls the position and rotation of the printhead, the bio-ink delivery, and the firing of the print nozzles.

Disclosed herein, in some embodiments, is a system comprising a controller and a printhead, wherein the printhead comprises a two-dimensional array of print nozzles. In some embodiments, the system comprises a controller. In some embodiments, the controller comprises a controller tip. In some embodiments, the controller tip comprises a printhead. In some embodiments, the printhead comprises a print nozzle. In some embodiments, the printhead comprises a plurality of print nozzles. In some embodiments, the printhead comprises a two-dimensional array of a plurality of print nozzles. In some embodiments, the system comprises a controller to control the printhead. In some embodiments, the controller is hand-held or mountable. In some embodiments, the controller is wireless. In some embodiments, the controller controls printhead parameters selected from: temperature; back-pressure; drops per nozzle; frequency of drop rate; number of nozzles in use; and firing energy, or a combination thereof. In some embodiments, the controller controls resolution, viscosity, cell concentration, physiological temperature and speed of printing. In some embodiments, the controller controls firing energy. In some embodiments, the firing energy comprises pulse energy, pulse width, length of gap between pulses, and voltage. In some embodiments, the printhead or controller further comprises a temperature control apparatus. Referring to FIG. 5, in some embodiments, the computer system further comprises a computer system. In some embodiments, the computer system comprises a processor, a memory device, an operating system, a software module for applying a diagnostic or a therapeutic analysis, and a software module for monitoring or operating an apparatus for dispensing bioink. In some embodiments, the computer system comprises a digital processing device and includes one or more hardware central processing units (CPU) that carry out the controllers' functions. In further embodiments, the system includes an operating system configured to perform executable instructions. In some embodiments, the operating system is software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. In some embodiments, the system includes a storage and/or memory device. In some embodiments, the storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the device is a storage device including, by way of non-limiting examples, CD-ROMs, DVDs, flash memory devices, magnetic disk drives, magnetic tapes drives, optical disk drives, and cloud computing based storage. In some embodiments, the storage and/or memory device is a combination of devices such as those disclosed herein. In some embodiments, the systems described herein include user interfaces. In further embodiments, the user interfaces include graphic user interfaces (GUIs). In still further embodiments, the user interfaces are interactive and present a user with menus and options for interacting with the systems and printheads described herein. In further embodiments, the system includes a display screen to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of displays such as those disclosed herein. In still further embodiments, the device includes an input device to receive information from a user. In some embodiments, the input device is a keyboard. In further embodiments, the input device is a key pad. In a particular embodiment, the input device is a simplified key pad for use by a subject with communications limitations (e.g., due to age, infirmity, disability, etc.), wherein each key is associated with a color, a shape, and health/communication concept. In some embodiments, the input device is a pointing device including, by way of non-limiting examples, a mouse, trackball, track pad, joystick, game controller, or stylus. In some embodiments, the input device is the display screen, which is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein. In some embodiments, the systems, and software modules disclosed herein are intranet-based. In some embodiments, the systems and software modules are Internet-based. In further embodiments, the systems and software modules are World Wide Web-based. In still further embodiments, the systems and software modules are cloud computing-based. In other embodiments, the systems and software modules are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof. In some embodiments, the system comprises an apparatus for dispensing bioink. In some embodiments, the system comprises a bio-ink delivery system and robotic arm. In some embodiments, the systems, software, and methods described herein utilize the services of a healthcare provider. In some embodiments, a healthcare provider is live. As used herein, the term "live" describes a human healthcare provider, as opposed to an artificial intelligence or a software algorithm, who interacts with the systems, devices, software, and/or subject described herein asynchronously, substantially synchronously, or synchronously (e.g., in real-time). In some embodiments, the healthcare provider is selected from a medical doctor, a dentist, a physician assistant, a nurse practitioner, a registered nurse, a chiropractor, an emergency medical technician, a licensed practical nurse, a certified ultrasound technician or a military medic. In some embodiments, the healthcare provider has had no formal medical training. In some embodiments, the systems, software, and methods described herein utilize the services of a plurality of healthcare providers. In further embodiments, a plurality of healthcare providers includes 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500 or more providers, including increments therein. In some embodiments, the systems, devices, software, and methods described herein utilize the services of at least 2, 3, 4, 5, 6, 7, 8, 9, 10, 11, 12, 13, 14, 15, 16, 17, 18, 19, 20 or more healthcare providers. In further embodiments, a plurality of healthcare providers use the systems simultaneously. In still further embodiments, a healthcare provider is identified or selected for a particular case or contact based on parameters including, by way of non-limiting examples, a patient's condition, disease, or injury, severity of a patient's condition, disease, or injury, a patient's insurance eligibility, or availability. In some embodiments, a healthcare provider is remote. As used herein, the term "remote" describes a healthcare provider who is not present with a subject at the time healthcare services are rendered using the inventions described herein. In some embodiments, a remote healthcare provider is outside of the facility, city, county, state, or country of the subject at the time healthcare services are rendered using the inventions described herein. In some embodiments, the systems disclosed herein optionally operate in an unsupervised, or automated, mode. In some embodiments, the system comprises a module for remote monitoring or operation by a telemedical care provider. In some embodiments, the systems, software, and methods described herein do not utilize the services of a live healthcare provider. For example, in some embodiments, the systems described herein include a non-communication mode, described further herein. In further embodiments, the systems and devices described herein operate in a non-communication mode when communication protocols fail, when communication channels or signals fail or are lost, or when devices are placed in a location where one or more communication protocols, channels, or signals are unavailable. In a non-communication mode, a live, remote healthcare provider is unable to monitor, supervise, or operate components of the system. By way of further example, in some embodiments, the systems described herein include an emergency mode, described further herein. In an emergency mode, in some embodiments, components of a system act autonomously, without monitoring, supervision, or operation by a live, remote healthcare provider. In some embodiments, the system comprises a biosensor. In some embodiments, the biosensor detects information about a tissue defect. In some embodiments, an healthcare provider programs information about a tissue defect into the controller. In some embodiments, an healthcare provider programs information about a tissue defect into the computer. In some embodiments, the information about the tissue defect comprises shape, size dimension, thickness, density or proximity of the tissue defect. In some embodiments, the, systems disclosed herein are employed, in part or in whole, in healthcare facilities such as hospitals, hospice, nursing homes, urgent care offices, diagnostic laboratories, and the like. In some embodiments, the devices, systems, and software are employed, in part or in whole, in veterinary facilities such as animal hospitals, veterinary offices, and the like. The systems disclosed herein, in some embodiments, employ an ink-jet system. In some embodiments, the ink-jet system is a thermal ink-jet system. In some embodiments, the ink jet system is a piezoelectric ink jet system. In some embodiments, the apparatus employs a syringe pump system. In some embodiments, the inkjet system comprises a heating element in each print nozzle. In some embodiments, the heating element raises the local print nozzle temperature to about 100 degrees, about 150 degrees, about 200 degrees, about 250 degrees, about 260 degrees, about 270 degrees, about 280 degrees, about 285 degrees, about 290 degrees, about 295 degrees, about 298 degrees, about 300 degrees, about 302 degrees, about 305 degrees, about 310 degrees, about 315 degrees, about 320 degrees, about 325 degrees, about 350 degrees, about 375 degrees, or about 400 degrees. In some embodiments, the heating element raises the local nozzle temperature to about 300 degrees. In some embodiments the heating element raises the temperature of the plurality of cells in the bio-ink about 1 degree, about 2 degrees, about 3 degrees, about 4 degrees, about 5 degrees, about 6 degrees, about 7 degrees, about 8 degrees, about 9 degrees, about 10 degrees, about 11 degrees, about 12 degrees, about 13 degrees, about 14 degrees or about 15 degrees. In some embodiments, the temperature of the plurality of cells in the bio-ink is raised for less than about 1 μsec, about 2 μsec, about 3 μsec, about 4 μsec, about 5 μsec, about 6 μsec, about 7 μsec, about 8 μsec, about 9 μsec or about 10 μsec.

Disclosed herein, in some embodiments, is a printhead comprising a two-dimensional array of print nozzles. In some embodiments, the printhead implements the methods disclosed herein. Existing printheads either use a single nozzle that is moved in two-dimensions to print a single droplet at a time or a linear array of nozzles that are moved in one-dimension in order to print a two-dimensional area. In some embodiments, the printheads disclosed herein do not require movement of the printhead if the two-dimensional array of print nozzles is equal to or larger than the two-dimensional area. In some embodiments, the printhead is a modified inkjet printhead. In some embodiments, the inkjet printhead is a thermal inkjet printhead. In some embodiments, the inkjet printhead is a piezoelectric inkjet printhead. In some embodiments, the printhead is a modified printhead selected from a Brother printhead, an Epson printhead, a Hewlett-Packard (HP) printhead, a Lexmark printhead, a Dymo printhead, an Oki printhead, a Premium Compatibles printhead, a Primera printhead, a Ricoh printhead, a Star Micronics printhead, a Vu Point printhead, a Wasp printhead or a Xerox printhead. In some embodiments, the printhead is modified from a printhead selected from a HP Deskjet printhead, a HP Officejet printhead, a HP Photosmart printhead. In some embodiments, the printhead is a modified printhead selected from a Deskjet 1000 Printhead, Deskjet 3000 Printhead, Deskjet 3050A Printhead All-in-One, DeskJet (original), DeskJet Plus, DeskJet Portable, Deskjet 200cci, DeskJet 300j, Deskjet 310/310 with Sheetfeeder, Deskjet 320/320 with Sheetfeeder, Deskjet 340/340cbi/340 cm/340cv, Deskjet 350c/350cbi, Deskjet 400/400L, Deskjet 420/420c, Deskjet 450cbi/450vci/450wbt, Deskjet 460c, Deskjet 460cb, Deskjet 460wf, Deskjet 460wbt, Deskjet 500/500c/500k, Deskjet 505d/505k, Deskjet 510, Deskjet 520, DeskJet 525q, Deskjet 540, Deskjet 550c, Deskjet 560c/560j/560k, Deskjet 600/600c/600k, Deskjet 610c/610c1, Deskjet 612c, Deskjet 630c, Deskjet 632c, Deskjet 640c/640u, Deskjet 642c, Deskjet 648c, Deskjet 656c/656cvr, Deskjet 660c/660cse/660k, Deskjet 670c/670k/670tv, Deskjet 672c, Deskjet 680c, Deskjet 682c, Deskjet 690c, Deskjet 692c/692k, Deskjet 693c, Deskjet 694c, Deskjet 695c/695cci, Deskjet 697c, Deskjet 710c, Deskjet 712c, Deskjet 720c, Deskjet 722c, Deskjet 810c, Deskjet 812c, Deskjet 815c, Deskjet 820cse/820cxi, Deskjet 825c/825cvr, Deskjet 830c, Deskjet 832c, Deskjet 840c, Deskjet 841c, Deskjet 842c, Deskjet 843c/843cxe, Deskjet 845c/845cv/845cvr, Deskjet 850c/850k, Deskjet 855c/855cse/855cxi, Deskjet 870cse/870cxi/870k, Deskjet 880c, Deskjet 882c, Deskjet 890c/890cse, Deskjet 895cse/895cxi, Deskjet 916c, Deskjet 920c/920cvr/920cxi, Deskjet 930c/930 cm, Deskjet 932c, Deskjet 934c, Deskjet 935c, Deskjet 940c/940cvr/940cw/940cxi, Deskjet 948c, Deskjet 950c, Deskjet 952c, Deskjet 955c, Deskjet 957c, Deskjet 959c, Deskjet 960c/960cse/960cxi, Deskjet 970cse/970cxi, Deskjet 980cxi, Deskjet 990 cm/990cse/990cxi, Deskjet 995c/995ck, Deskjet 1000cse/1000cxi, Deskjet 1100c, Deskjet 1120c/1120cse/1120cxi, Deskjet 1125c, Deskjet 1180c, Deskjet 1200c/1200c/PS, Deskjet 1220c/1220c/PS/1220cse/1220cxi, Deskjet 1280, Deskjet 1600c/1600 cm/1600cn, Deskjet 3320/3322/3323 3325, Deskjet 3420/3425/3450, Deskjet 3520/3535/3550, Deskjet 3620/3645/3648/3650/3653, Deskjet 3740/3743/3744/3745/3747/3748, Deskjet 3810/3816/3820/3822/3843/3845/3847/3848, Deskjet 3910/

3915/3918/3920/3930/3938/3940, Deskjet 5145/5150/5155/ 5160, Deskjet 5420v/5440/5442/5443, Deskjet 5550/5551/ 5552, Deskjet 5650/5650w/5652/5655, Deskjet 5740/5743/ 5745/5748, Deskjet 5850, Deskjet 5940/5943, Deskjet 6122/ 6127, Deskjet 6520/6540/6543/6548, Deskjet 6620, Deskjet 6830v/6840/6843/6848, Deskjet 6940/6980, Deskjet 6988, Deskjet 6988dt, Deskjet 9300, Deskjet 9650/9670/9680, Deskjet 9800/9800d, Deskjet D1455, Deskjet D1520, Deskjet D1560, Deskjet D2400, Deskjet D2430, Deskjet D2460, Deskjet D2530, Deskjet D2545, Deskjet D2560, Deskjet D2660, Deskjet D4160, Deskjet D4260, DeskJet F380 All-in-One, DeskJet F4100 series All-in-One, DeskJet F4200 series All-in-One or DeskJet F4580 All-in-One. In some embodiments the printhead is a modified Hewlett-Packard (HP) Deskjet 500 thermal inkjet printhead. In some embodiments, the printhead is a modified custom printhead. In some embodiments, the printhead is a custom printhead produced for bioprinting. In some embodiments, the printhead is a modified laser printhead. In some embodiments, the printhead comprises at least one nozzle. In some embodiments, the printhead comprises at least 5 nozzles. In some embodiments, the printhead comprises about 6-20 nozzles per tip. In some embodiments, the printhead comprises 10, 12 or 16 nozzles. In some embodiments, the printhead comprises about 5, about 10, about 15, about 20, about 25, about 30, about 35, about 40, about 45, about 50, about 55, about 60, about 65, about 70, about 75, about 80, about 85, about 90, about 95 or about 100 nozzles. In some embodiments the diameter of the nozzle is about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 105 µm, about 110 µm, about 115 µm, about 120 µm, about 125 µm, about 130 µm, about 135 µm, about 140 µm, about 145 µm, or about 150 µm. In some embodiments, the diameter of the nozzle is about 120 µm. In some embodiments, the diameter of the nozzle is less than about 120 µm. In some embodiments, the diameter of the nozzle is greater than 120 µm. In some embodiments, the nozzles are arranged in one row of nozzles. In some embodiments, the nozzles are not arranged in a row of nozzles. In some embodiments, the nozzles are arranged in two rows of nozzles. In some embodiments, the nozzles are arranged in about 3, 4, 5, 6, 7, 8, 9, 10, 15, 20, 25, 30, 35, 40, 45, or 50 rows of nozzles. In some embodiments, the nozzles are arranged in two rows of 10, 12 or 16 nozzles. In some embodiments, each row of nozzles has the same number of nozzles. In some embodiments, one or more rows of nozzles have a different number of nozzles from one or more other rows. In some embodiments, the length of the rows is described as the Y-axis of the row. In some embodiments, the Y-axis spacing between print nozzles in a row of print nozzles is between about 5 micrometers and about 500 micrometers. In some embodiments, the Y-axis spacing between print nozzles in a row of print nozzles is between about 5 micrometers and about 200 micrometers, between about 5 micrometers and about 100 micrometers, between about 50 micrometers and about 200 micrometers, between about 1 micrometer and about 50 micrometers, or between about 200 micrometers and about 400 micrometers. In some embodiments, the Y-axis spacing between print nozzles in a row of nozzles is between about 200 micrometers and about 400 micrometers. In some embodiments, the spacing between rows of print nozzles is between about 5 micrometers and about 500 micrometers. In some embodiments, the spacing between rows of print nozzles is between about 5 micrometers and about 200 micrometers, between about 5 micrometers and about 100 micrometers, between about 50 micrometers and about 200 micrometers, between about 1 micrometer and about 50 micrometers, or between about 200 micrometers and about 400 micrometers. In some embodiments, the spacing between rows of print nozzles is between about 200 micrometers and about 400 micrometers. In some embodiments of 10 nozzles arranged in two rows, the Y-axis spacing between nozzles is about 20 dpi, about 30 dpi, about 40 dpi, about 60 dpi, about 70 dpi, about 80 dpi, about 90 dpi, about 100 dpi, about 110 dpi, about 120 dpi, about 130 dpi, about 140 dpi, about 150 dpi, about 160 dpi, about 170 dpi, about 180 dpi, about 190 dpi, about 200 dpi, about 250 dpi or about 300 dpi. In some embodiments of 10 nozzles arranged in two rows, the Y-axis spacing between nozzles is about 150 dpi. In some embodiments, the spacing between rows is about 200 µm, about 220 µm, about 240 µm, about 260 µm, about 280 µm, about 300 µm, about 320 µm, about 340 µm, about 360 µm, about 380 µm, about 400 µm, about 420 µm, about 450 µm, or about 500 µm. In some embodiments, the spacing between rows is about 340 µm. In some embodiments of 12 nozzles arranged in two rows, the Y-axis spacing between nozzles is about 20 dpi, about 30 dpi, about 40 dpi, about 60 dpi, about 70 dpi, about 80 dpi, about 90 dpi, about 100 dpi, about 110 dpi, about 120 dpi, about 130 dpi, about 140 dpi, about 150 dpi, about 160 dpi, about 170 dpi, about 180 dpi, about 190 dpi, about 200 dpi, about 250 dpi or about 300 dpi. In some embodiments of 12 nozzles arranged in two rows, the Y-axis spacing between nozzles is about 180 dpi or 141 µm. In some embodiments, the spacing between rows is about 200 µm, about 220 µm, about 240 µm, about 260 µm, about 280 µm, about 300 µm, about 320 µm, about 340 µm, about 360 µm, about 380 µm, about 400 µm, about 420 µm, about 450 µm, or about 500 µm. In some embodiments, the spacing between rows is about 300 µm. In some embodiments of 16 nozzles arranged in two rows, the Y-axis spacing between nozzles is about 20 dpi, about 30 dpi, about 40 dpi, about 60 dpi, about 70 dpi, about 80 dpi, about 90 dpi, about 100 dpi, about 110 dpi, about 120 dpi, about 130 dpi, about 140 dpi, about 150 dpi, about 160 dpi, about 170 dpi, about 180 dpi, about 190 dpi, about 200 dpi, about 250 dpi, about 300 dpi, about 320 dpi, about 340 dpi, about 360 dpi, about 380 dpi, about 400 dpi, about 450 dpi or about 500 dpi. In some embodiments of 16 nozzles arranged in two rows, the Y-axis spacing between nozzles is about 300 dpi or 84 µm. In some embodiments, the spacing between rows is about 200 µm, about 220 µm, about 240 µm, about 260 lam, about 280 µm, about 300 µm, about 320 µm, about 340 µm, about 360 µm, about 380 µm, about 400 µm, about 420 µm, about 450 µm, or about 500 µm. In some embodiments, the spacing between rows is about 230 µm. Referring to FIG. 3, in some embodiments, the printhead comprises a configuration of print nozzles. In some embodiments, the configuration of print nozzles comprises parallel print nozzles. In some embodiments, the configuration comprises non-parallel print nozzles. In some embodiments, the configuration comprises converging print nozzles. In some embodiments, the configuration comprises diverging print nozzles. In some embodiments, the print nozzles are positioned at a level above or at the substrate. In some embodiments, the level is changed so as to increase or decrease proximity of the print nozzle and the substrate without moving the printhead. In some embodiments, the configuration comprises print nozzles with the level of the print nozzles all in the same plane. In some embodiments, the configuration comprises print nozzles with the level of one or more print nozzles not in the same plane. In some embodiments, one or more configurations are combined. In some embodiments, the configuration of print nozzles comprises a print nozzle, wherein the direction of the print nozzle is modular. In some embodiments, the print nozzle permits drop volumes of bio-ink ejected from a printhead between about 2 picoliters and about 220 picoliters. In some embodiments, a bio-ink drop is about 1 pL, about 2 pL, about 5 pL, 10 pL, about 15 pL, about 20 pL, about 25 pL, about 30 pL, about 35 pL, about 40 pL, about 45 pL, about 50 pL, about 55 pL, about 60 pL about 65 pL, about 70 pL, about 75 pL, about 80 pL, about 85 pL, about 90 pL, about 95 pL, about 100 pL, about 105 pL, about 110 pL, about 115 pL, about 120 pL, about 125 pL, about 130 pL, about 135 pL, about 140 pL, about 145 pL, about 150 pL, about 155 pL, about 160 pL, about 165 pL, about 170 pL, about 175 pL, about 180 pL, about 185 pL, about 190 pL, about 195 pL, about 200 pL, about 250 pL, about 300 pL, about 500 pL, or about 1 nL. In some embodiments, the printhead has a resolution of at least about 100 dots per inch (dpi). In some embodiments, the printhead has a resolution of at least about 150 dpi, at least about 200 dpi, at least about 300 dpi, at least about 400 dpi, at least about 500 or more dpi, or about 1000 or more dpi. In some embodiments, the print nozzles fire with a frequency of about 1000 Hz, about 1200 Hz, about 1400 Hz, about 1600 Hz, about 1800 Hz, about 2000 Hz, about 2200 Hz, about 2400 Hz, about 2600 Hz, about 2800 Hz, about 3000 Hz, about 3200 Hz, about 3400 Hz, about 3600 Hz, about 3800 Hz, about 4000 Hz, about 4200 Hz, about 4400 Hz, about 4600 Hz, about 5000 Hz, about 5200 Hz, about 5400 Hz, about 5600 Hz, about 5800 Hz, or about 6000 Hz.

Disclosed herein, in certain embodiments, are methods of direct manufacturing of a tissue or portion thereof within a tissue defect of a patient, comprising i) positioning a printhead comprising a two-dimensional array of print nozzles within proximity of the tissue defect; and ii) ejecting a bio-ink comprising cells onto the tissue defect to produce a manufactured tissue in the tissue defect. Advantages of printing directly onto a tissue defect include, but are not limited to: i) eliminating the need for prior manufacturing, storage, or transportation; ii) providing the ability to customize the engineered tissue to perfectly fit defects of any shape or size; iii) the ability to vary the type or amount of tissue being generated during surgery; iv) the ability to combine artificial and natural scaffolds as well as living cells; and v) enabling direct integration of the newly printed tissue into the host tissue. In some embodiments, the patient is a burn victim, an athlete or an amputee. In some embodiments, the patient is an elderly individual, an infant or a youth. In some embodiments, the patient is in need of an organ transplant. In some embodiments, the patient in need of an organ transplant requires an eye, a heart, a lung, a stomach, an intestine, a colon, a bladder, a pancreas, a spleen, a uterus, an ovary, a prostate, a muscle, a bone, an artery, a blood vessel, a thyroid, a liver or a kidney. In some embodiments, the patient suffers from an autoimmune disease, a cardiovascular disorder, an autophageal disorder or a neurodegenerative disorder. In some embodiments, the neurodegenerative disorder is selected from Parkinson's Disease, Alzheimer's Disease, Huntington's Disease, Amyotrophic Lateral Sclerosis (Lou Gehrig's Disease), or macular degeneration. In some embodiments, the autoimmune disease is selected from multiple sclerosis, encephalomyelitis, hepatitis, inner ear disease, peripheral neuropathy or pancreatitis. In some embodiments, the patient is suffering from brain trauma, tissue degeneration, cancer, arthritis, osteoarthritis, gout, tooth decay or an ulcer. In some embodiments, subject suffers from osteoarthritis. In some embodiments, the patient is a human. In some embodiments, the patient is a non-human animal veterinary patient. In further embodiments, a non-human animal veterinary patient is under the care of an owner, caretaker, rescuer, or veterinarian. In still further embodiments, a non-human animal veterinary patient includes, by way of non-limiting example, those attended to by exotic animal veterinarians, large animal veterinarians, domestic animal veterinarians, wildlife veterinarians, laboratory animal veterinarians, food animal veterinarians, and equine veterinarians. In still further embodiments, a non-human animal veterinary patient includes, by way of non-limiting example, those classified as invertebrates, fish, amphibians, reptiles, birds, and mammals. In some embodiments, the manufactured tissue is in an ear, an eye, a cornea, a nose, a brain, a sinus, a tooth, a bone, cartilage, skin, an esophagus, a trachea, a *thymus*, a thyroid, a heart, a blood vessel, an aorta, an artery, a lung, a diaphragm, a lymph node, a breast, a nipple, a stomach, an intestine, a colon, a rectum, a pancreas, a spleen, a bladder, a kidney, a liver, an ovary, a uterus, a vagina, a prostate, a penis, a cervix, adipose, skin, cartilage, skeletal muscle, smooth muscle or a portion thereof. In some embodiments, the tissue defect is located in or on a tissue or organ selected from a vascular tissue, an osteochondral tissue, an epidermal tissue, a muscular tissue, an intestinal tissue, a neuronal tissue, a reproductive tissue, a pancreatic tissue, an ocular tissue, an ear, an eye, a cornea, a nose, a brain, a sinus, a tooth, a bone, cartilage, skin, an esophagus, a trachea, a *thymus*, a thyroid, a heart, a blood vessel, a lung, a diaphragm, a lymph node, a breast, a nipple, a stomach, an intestine, a colon, a rectum, a pancreas, a spleen, a bladder, a kidney, a liver, an ovary, a uterus, a vagina, a prostate, a penis, a cervix, adipose, skeletal muscle, smooth muscle or skin. In some embodiments, the skin is located on a head, on a face, on a neck, on a shoulder, on a chest, on an arm, on a hand, on a back, on a buttock, on a leg, on an ankle or on a foot. In some embodiments, the method further comprises treating a tissue defect in a joint. In some embodiments, the joint is located in a neck, a shoulder, a back, a spine, a chest, an arm, a hand, an elbow, a wrist, a finger, a leg, an ankle, a foot, a hip or a knee. In some embodiments, the joint is located in a knee. In some embodiments, the method further comprises treating a tissue defect, wherein the tissue defect comprises a birth defect or a congenital defect. In some embodiments, tissue defect is a result of an injury. In some embodiments, the injury is due to musculoskeletal trauma, a sport injury, an automobile accident, an infection or a tumor. In some embodiments, the method further comprises treating a tissue defect wherein the tissue defect is selected from a damaged tissue, eroded tissue, diseased tissue or degenerated tissue. In some embodiments, the damaged tissue is selected from a tissue damaged by a burn, an abrasion, a tear, a lesion, a break, a fracture, a bruise, a hematoma, a scratch, a cut, a puncture, an infection, a tumor, frostbite, overuse or necrosis. In some embodiments, the method further comprises characterization of the tissue defect. In some embodiments, the method comprises x-ray, CAT/CT scan, PET scan, MRI, ultrasound, thermography, endoscopy, radiography or biopsy of the tissue defect. In some embodiments, the method further comprises preparation of the tissue defect before surgery. In some embodiments, preparation of the tissue defect comprises tissue removal, radiation, sterilization, cleaning, treatment with an antibiotic or treatment with an anaesthetic.

EXAMPLES

Example 1

Printing a Tissue with a Two-Dimensional Array Printhead

Osteochondral plugs are harvested from bovine femoral condyles under aseptic conditions in order to serve as substrate for printing. The plugs are cultured in DMEM supplemented with 10% calf serum. Purified poly(ethylene glycol)dimethacrylate (PEGDMA, 3400 MW) is dissolved in PBS or deionized water to a final concentration of 10% and 20% weight/volume (w/v). Alternatively, PEGDMA is dissolved in tetrahydrofuran and reacted with methacryloyl chloride in the presence of triethylamine overnight under nitrogen. Photoinitiator 1-2959 is added to a final concentration of 0.05% w/v to provide a cytocompatible photoinitiating condition. Human articular chondrocytes are suspended in filter-sterilized PEGDMA solution at a concentration of $5 \times 10^6$ cells/mL.

Isolation of Primary Human Chondrocytes

Healthy human articular cartilage is rinsed and sterilized with phosphate buffered saline (PBS). Sterile scalpels are used to excise articular cartilage from femoral condyles and tibia plateaus under aseptic conditions. Harvested cartilage samples are minced and treated with 0.5 mg/mL trypsin at 37° C. for 15 min. After removing trypsin solution, the cartilage tissues are digested with 2 mg/mL type IV clostridial collagenase in DMEM with 5% fetal calf serum for 12 h to 16 h at 37° C. Released human articular chondrocytes are washed three times with DMEM supplemented with 1× penicillin-streptomycin-glutamine (PSG) and cell viability is determined. Isolated chondrocytes are seeded into T175 tissue culture flasks at 5 million cells per flask for expansion in monolayer and cultured in DMEM supplemented with 10% calf serum and 1×PSG. Cells are incubated at 37° C. with humidified air containing 5% $CO_2$. The culture medium is changed every 4 days. Human chondrocytes are ready to be used (e.g. bioprinted) when 80% to 90% confluence is reached (1 to 2 weeks in primary culture). All cells used for bioprinting are first or second passage.

A bioprinting platform with a two-dimensional printhead of 300 dots or nozzles per square inch is set at a distance of 1 to 2 mm from the substrate. Patterns with the shape and size of the cartilage defect of mold are designed using Adobe Photoshop and printed layer by layer to fabricate a three-dimensional construct. Printed cell-hydrogel constructs are cultured with DMEM supplemented with 1× insulin-transferrin-selenium, 0.1 mM ascorbic acid 2-phosphate, 1.25 mg/ml human serum albumin, $10^{-7}$ M dexamethasone, 1×PSG, and 10 ng/mL TGF-β1 to maintain chondrogenic phenotype of the chondrocytes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are employed in practicing the invention. It is intended that the following claims define the scope of the invention and that methods and structures within the scope of these claims and their equivalents be covered thereby.

What is claimed is:

1. A method of printing a bio-ink layer onto a tissue defect, comprising:
   i) positioning a printhead comprising a plurality of rows comprising a plurality of print nozzles, such that at least one print nozzle of the plurality of print nozzles is within 5 cm of the tissue defect;
   ii) ejecting a bio-ink through the at least one print nozzle onto the tissue defect without movement of the printhead relative to the tissue defect, thereby forming a bio-ink layer,
   wherein the plurality of print nozzles is configured to be positioned at varying heights; and
   iii) repeating step ii a plurality of times without moving the printhead relative to the tissue defect between repeated steps,
   wherein the tissue defect comprises a vascular defect, an osteochondral defect, an epidermal defect, a muscular defect, an intestinal defect, a neuronal defect, a reproductive defect, a pancreatic defect, an ocular defect, or any combination thereof.

2. The method of claim 1, wherein the bio-ink layer comprises a plurality of bio-ink layers.

3. The method of claim 1, wherein the at least one print nozzle is independently actuated to print an individual droplet.

4. The method of claim 1, wherein the plurality of print nozzles is fired simultaneously.

5. The method of claim 1, wherein the plurality of print nozzles is fired in a specified sequence.

6. The method of claim 1, wherein a spacing between a first print nozzle and a second print nozzle of the plurality of print nozzles is between 5 micrometers and 500 micrometers.

7. The method of claim 1, wherein the printhead is mounted on a robotic arm for positioning the printhead relative to the tissue defect.

8. The method of claim 7, further comprising controlling the robotic arm by a computer system.

9. The method of claim 1, wherein the printhead comprises a piezoelectric ink-jet printhead.

10. The method of claim 1, wherein the plurality of print nozzles is mounted in fixed positions relative to one another.

11. The method of claim 1, wherein the printhead comprises an area that greater than an area of the tissue defect.

12. The method of claim 1, wherein a diameter of the at least one print nozzle is between 5 micrometers and 150 micrometers.

13. The method of claim 12, wherein the diameter of the at least one print nozzle is between 120 micrometers and 150 micrometers.

14. The method of claim 1, further comprising blocking a portion of the plurality of print nozzles from ejecting the bio-ink by applying a mask.

15. The method of claim 1, wherein ejecting the bio-ink from the at least one print nozzle comprises ejecting a volume of bio-ink that is between 1 picoliter and 1 nanoliter.

16. The method of claim 1, wherein the plurality of print nozzles is in a parallel configuration.

17. The method of claim 1, wherein the plurality of print nozzles is in a diverging configuration.

18. The method of claim 1, wherein the plurality of print nozzles is in a non-parallel configuration that corresponds to the tissue defect's area.

19. The method of claim 1, wherein the plurality of print nozzles is not in the same plane and a pattern of the plurality of print nozzles is customized to the tissue defect's pattern.

20. The method of claim 1, wherein an individual print nozzle of the plurality of print nozzles is configured to be at an angle to another individual print nozzle.

21. A method of printing a bio-ink layer onto a tissue defect, comprising:
   i) positioning a printhead comprising a plurality of rows comprising a plurality of print nozzles, such that at least one print nozzle of the plurality of print nozzles is within 5 cm of the tissue defect;
   wherein said positioning of the printhead is maintained by a robotic arm;
   ii) ejecting a bio-ink through the at least one print nozzle directly onto the tissue defect without movement of the printhead relative to the tissue defect, thereby forming a bio-ink layer,
   wherein the plurality of print nozzles is configured to be positioned at varying heights; and
   iii) repeating step ii a plurality of times without moving the printhead relative to the tissue_defect between repeated steps,
   wherein the tissue defect comprises a vascular defect, an osteochondral defect, an epidermal defect, a muscular defect, an intestinal defect, a neuronal defect, a reproductive defect, a pancreatic defect, an ocular defect, or any combination thereof.

22. The method of claim 21, wherein an individual print nozzle of the plurality of print nozzles is configured to be at an angle to another individual print nozzle.

23. A method of printing a bio-ink layer onto a tissue defect, comprising:
   i) positioning a printhead comprising a plurality of rows comprising a plurality of print nozzles, such that at least one print nozzle of the plurality of print nozzles is within 5 cm of the tissue defect;
   ii) ejecting a bio-ink through the at least one print nozzle directly onto the tissue defect without movement of the printhead relative to the tissue defect, thereby forming a bio-ink layer,
   wherein the plurality of print nozzles is configured to be positioned at varying heights; and
   iii) repeating step ii a plurality of times without moving the printhead relative to the tissue defect between repeated steps; and
   wherein the plurality of print nozzles are not in the same plane and the a pattern of the plurality of print nozzles is customized to the tissue defect's pattern, and
   wherein the tissue defect comprises a vascular defect, an osteochondral defect, an epidermal defect, a muscular defect, an intestinal defect, a neuronal defect, a reproductive defect, a pancreatic defect, an ocular defect, or any combination thereof.

24. The method of claim 23, wherein an individual print nozzle of the plurality of print nozzles is configured to be at an angle to another individual print nozzle.

* * * * *